(12) United States Patent
Patel et al.

(10) Patent No.: US 12,114,873 B1
(45) Date of Patent: *Oct. 15, 2024

(54) TRIAL SIZER FOR ALIGNMENT OF PILOT HOLES

(71) Applicant: The Regents of the University of Colorado, a Body Corporate, Denver, CO (US)

(72) Inventors: Vikas Patel, Denver, CO (US); Leighton Joseph LaPierre, Hampstead, NC (US); Brandon Blair Arthurs, Wilmington, NC (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/206,373

(22) Filed: Jun. 6, 2023

Related U.S. Application Data

(63) Continuation of application No. 17/072,995, filed on Oct. 16, 2020, now Pat. No. 11,806,030.

(60) Provisional application No. 62/915,679, filed on Oct. 16, 2019.

(51) Int. Cl.
*A61B 17/17* (2006.01)
(52) U.S. Cl.
CPC ...... *A61B 17/1757* (2013.01); *A61B 17/1728* (2013.01)

(58) Field of Classification Search
CPC ............ A61B 17/1757; A61B 17/1728; A61B 17/7059; A61B 17/8872
See application file for complete search history.

(56) References Cited

U.S. PATENT DOCUMENTS

| 8,932,358 | B1* | 1/2015 | Nehls ..................... | A61F 2/4455 |
| | | | | 623/17.16 |
| 9,375,237 | B2* | 6/2016 | Keegan ............... | A61B 17/1757 |
| 11,806,030 | B1* | 11/2023 | Patel ................... | A61B 17/8605 |
| 2016/0235448 | A1* | 8/2016 | Seex ..................... | A61B 17/808 |
| 2017/0340358 | A1* | 11/2017 | Bullard .............. | A61B 17/1757 |

* cited by examiner

*Primary Examiner* — Tracy L Kamikawa
(74) *Attorney, Agent, or Firm* — Nicholas Pfeifer; Smith & Hopen, P. A.

(57) ABSTRACT

A device and method for drilling a pilot hole within an object at a predetermined angle. The device includes a spacer having a lateral surface established by a first surface and a second surface and at least a portion of the lateral surface includes an extension. The extension having a proximal end and a distal end where the proximal end abuts the lateral surface and the distal end is configured to couple to a first end of a body. A guide body is also provided and is coupled to the device. The guide member includes a bore extending from a first end to a second end. Subsequent to disposing the spacer within the object, a drilling instrument may be disposed within the guide body thereby drilling out the pilot hole at the prescribed angle.

15 Claims, 20 Drawing Sheets

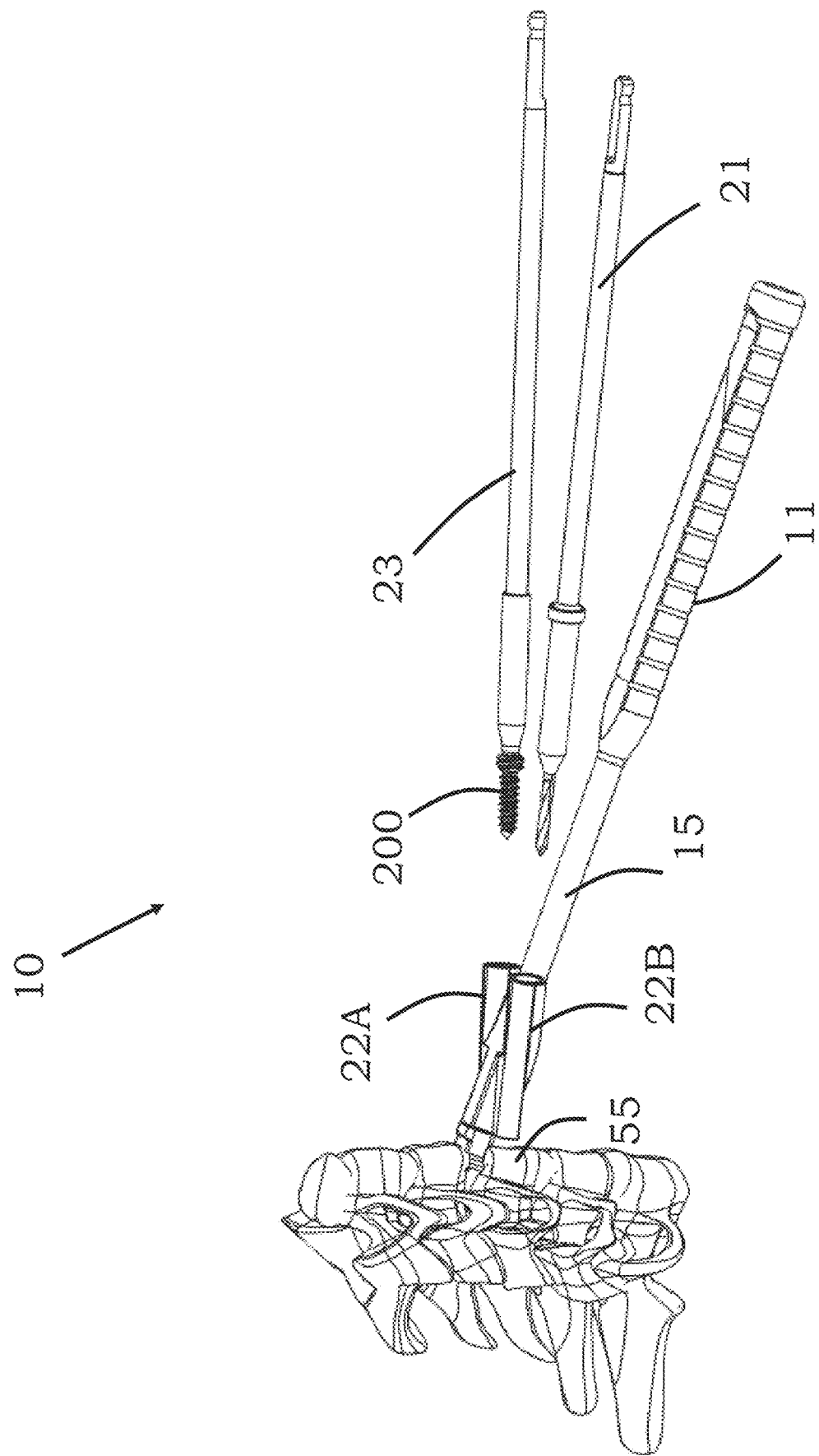

TRIAL SIZER FOR ALIGNMENT OF PILOT HOLES

CROSS-REFERENCE TO RELATED APPLICATIONS

This nonprovisional application is a continuation of and claims priority to nonprovisional application Ser. No. 17/072,995, now U.S. Pat. No. 11,806,030 entitled "TRIAL SIZER FOR ALIGNMENT OF PILOT HOLES," filed Oct. 16, 2020 by the same inventor(s), which claims priority to provisional application No. 62/915,679, entitled "TRIAL SIZER FOR ALIGNMENT OF PILOT HOLES," filed Oct. 16, 2019 by the same inventor(s).

BACKGROUND OF THE INVENTION

1. Field of the Invention

This invention relates, generally, to trial sizers for implantable orthopedic devices. More specifically, it relates to trial sizers used to align the placement of one or more fasteners prior to securing an implant, such as a vertebral column support plate.

2. Brief Description of the Prior Art

When a human or animal breaks or fractures a bone, the treatment sometimes includes positioning one or more interacting elements relative to the bone to stabilize said bone in an optimized position for healing. One or more interacting elements may include, for example, an implantable plate and one or more fastener elements for attachment of the plate to vertebrae in order to immobilize, stabilize and/or align those vertebrae. The plate may be used for a variety of conditions including, for example, providing added strength and rigidity after fusion of adjacent vertebrae, securing vertebrae together where an intervening vertebra has been removed and replaced, correcting spinal deformities, and correcting instability caused by trauma, fractures, tumors, advanced degenerative discs, infection, or congenital or acquired deformities.

Plates used for these types of conditions generally span the distance between two, three, four, or more vertebrae, as required in a given situation. The plates are generally curved to fit the curvature of the vertebrae to which they are attached and the curvature of the cervical spine. A plate of this type is also typically provided with holes for fastener elements known as "bone screws."

When these plates are implanted, pilot holes are drilled into the adjacent vertebrae by instruments that are known in the art, such as surgical drills. After which, the plate is attached to the vertebrae via the bone screws which are inserted into the pilot holes to engage the vertebrae. However, the existing methods and systems for drilling pilot holes are associated with certain disadvantages. For instance, there aren't any systems and methods to produce pilot holes that are consistently at the same angle, spacing, and depth to perfectly match the dimensions of the plate to be implanted. Thus, there is a demand for an improved system and method for drilling one or more pilot holes at a predetermined angle, spacing, and/or depth. The present invention satisfies this demand and provides an easy-to-use, quick pilot hole alignment guide with specific features not previously known Accordingly, what is needed is an improved trial sizer that provides quick and easy alignment for drilling one or more pilot holes at an angle that corresponds to an angle of fastener receipts in an implant. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved trail sizer and method of use is now met by a new, useful, and nonobvious invention.

An embodiment of the present invention includes a device for drilling one or more pilot holes and inserting fastener(s) into a patient's vertebrae. The device has a main body, which includes a handle, a spacer, and a guide body. The handle has a gripping section proximate to a proximal end of the main body. The spacer is located at a distal end of the main body, and a guide body is located between the spacer and the gripping section of the handle.

The spacer has a first surface and a second surface with a lateral edge extending therebetween, and a proximal end and a distal end with a longitudinal axis extending therebetween. Moreover, the spacer is sized to reside between two of the patient's vertebrae. In some embodiments, the spacer is temporarily attachable to the handle and/or the guide body. Some embodiments include a plurality of temporarily attachable spacers with different thicknesses extending between the first and second surfaces of each spacer. In addition, the first surface of each spacer is spaced the same distance from the distal ends of the hollow instrument guides. As a result, the pilot holes will be drilled at a consistent location on a vertebra regardless of the thickness of the spacer.

The guide body includes a pair of hollow instrument guides. Each hollow instrument guide includes a bore hole extending from a proximal end and a distal end. Each bore hole has a longitudinal axis extending therebetween. In some embodiments, the bore holes in the pair of hollow instrument guides are non-parallel to the longitudinal axis of the spacer. Some embodiments of the guide body further include a cutout window proximate the distal end of one or more hollow instrument guides. The cutout window provides a visual of any instruments within the hollow instrument guide prior to the instruments interacting with the patient's vertebrae. In addition, the cutout window allows an operator to confirm that the instrument is engaging the correct structure and determine when a fastener is partially secured in a patient's vertebra.

In some embodiments, each bore hole in the guide body has a diameter sized to receive a fastener intended for insertion into the patient's vertebrae. Thus, the fastener can be inserted through one of the bore holes in the hollow instrument guides to secure the fastener in the patient's vertebrae without having to first remove the device from the patient.

In some embodiments, the guide body can be removed from the main body. In some embodiments, the hollow instrument guides are angled towards each other moving in a distal direction.

In operation, the spacer can be inserted between two of the patient's vertebrae and the guide body provides a user with a hollow path through which a drilling instrument can be disposed to guide the user to a proper drilling location relative to the patient's vertebrae.

An embodiment of the present invention includes a novel method of implanting a device within a patient. The method includes providing a trial sizer. The trial sizer has a spacer secured to the distal end of a main body and the spacer has a first surface and a second surface with a lateral edge extending therebetween. The spacer is sized to reside between a patient's vertebrae.

The trial sizer also includes a guide body residing proximate to the spacer. The guide body includes a pair of hollow instrument guides. Each hollow instrument guide includes a bore hole extending from a proximal end and a distal end, with the bore holes each having a longitudinal axis extending therebetween. In some embodiments, the longitudinal axes of the bore holes in the pair of hollow instrument guides are non-parallel to the longitudinal axis of the main body and/or the longitudinal axis of the spacer.

The novel method further includes inserting the spacer into a cavity within the patient, such that the hollow instrument guides are angled towards a first vertebrae. Then a drilling instrument is inserted within at least one of hollow instrument guides and a pilot hole is drilled into the first vertebrae.

A first implantable interacting element and a second interacting element are also provided. The first implantable interacting element has a main body and a thread receipt. The second interacting element has a thread configured to engage the thread receipt of the first implantable element. The second interacting element is inserted into the pilot hole. In some embodiments, the step of inserting the second interacting element within the pilot hole includes only partially inserting the second interacting element into the pilot hole.

Then, the first implantable interacting element is positioned between a proximal end of the partially inserted second interacting element and the first vertebrae. Once first implantable interacting element is in place, the second interacting element is further inserted within the first vertebrae, such that the thread of the second interacting element engages the thread receipt of the first implantable interacting element, thereby securing the first implantable interacting element to the second interacting element.

Some embodiments further include the steps of rotating the trial sizer 180 degrees about the longitudinal axis of the spacer; inserting the spacer into the cavity within the patient, such that the hollow instrument guides are angled towards a second vertebrae in the patient; inserting the drill bit within the guide member and drilling additional pilot holes into the second vertebrae; removing the trial guide; and inserting additional second interacting elements within the additional pilot holes. The additional second interacting elements can then be further inserted within the second vertebrae, such that the threads of the additional second interacting elements engage additional thread receipts of the first implantable interacting element, thereby further securing the first implantable interacting to the second vertebrae.

In some embodiments, inserting the second interacting element into the pilot hole further includes inserting the second interacting element through one of the hollow instrument guides when the spacer is within the cavity within the patient.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 10 is a perspective view showing an embodiment of the trial sizer inserted between two vertebrae.

DETAILED DESCRIPTION OF THE INVENTION

Figure 1:
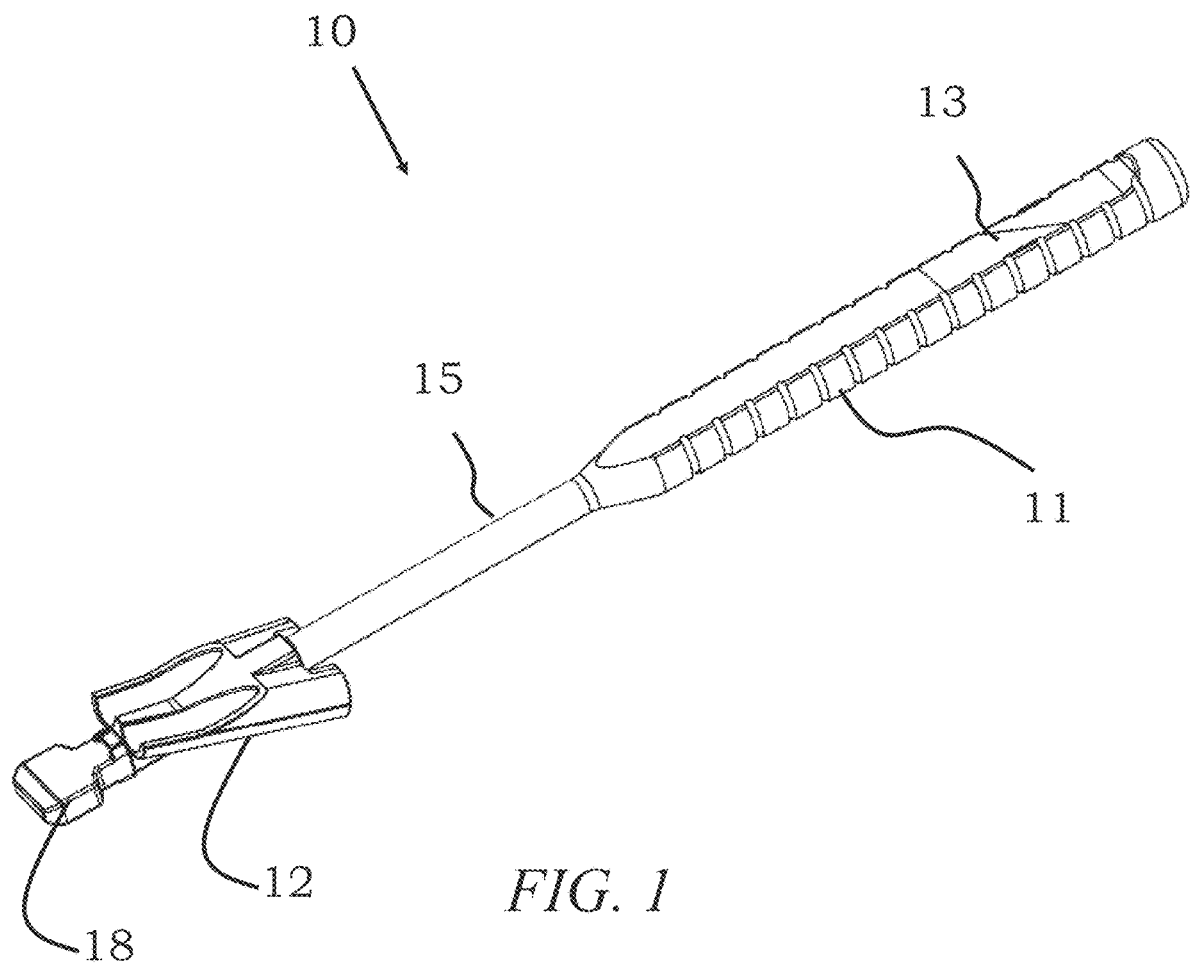
FIG. 1 illustrates a perspective view of an embodiment of the trial sizer.

For convenience of description, terms such as "above," "below," "upper," "lower," "outer," "inner," "bottom," and "top" are used in this application to refer to the system and the components of the system in an orientation illustrated in the accompanying drawings. However, it will be understood that the embodiments of the invention described in this application advantageously can be used in a variety of orientations.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

The present invention includes a novel trial sizer and method of use. The trial sizer is configured to assist in the drilling of one or more pilot holes within an object (e.g., the bone of the patient) by providing precise drilling angles and spacing for the one or more pilot holes.

Some embodiments include a multi-piece construction enabling the use of the spacer without the guides or allowing a surgeon to exchange one spacer for another spacer of a different thickness.

Some embodiments include cutout windows allowing the surgeon to visually identify (1) the depth of the drill, (2) the depth of the fasteners during insertion to ensure that the fasteners remains proud with respect to the bone insertion surface, and (3) that the drill bit and the screw are not penetrating surrounding tissue instead of the intended bone.

Some embodiments include the guides having an internal diameter sufficiently large to accommodate a fastener and a fastener driver, thereby allowing the fastener to be inserted into the pilot hole while the trial sizer remains in place.

Referring to FIGS. 1-5, an embodiment of the present invention includes trial sizer 10, which is comprised of handle section 11, guide body 12, and spacer 18. Handle section 11 includes gripping region 13 at its proximal end and shaft 15 extending from gripping region 13 in a distal direction towards guide body 12. Handle section 11 is used to position guide body 12 and/or spacer 18 into the proper position to perform the necessary surgical steps. In some embodiment, gripping region 13 includes a plurality of ridges, bumps, slots, or other features designed to increase the friction of gripping region 13 in both wet and dry conditions.

Figure 2A:
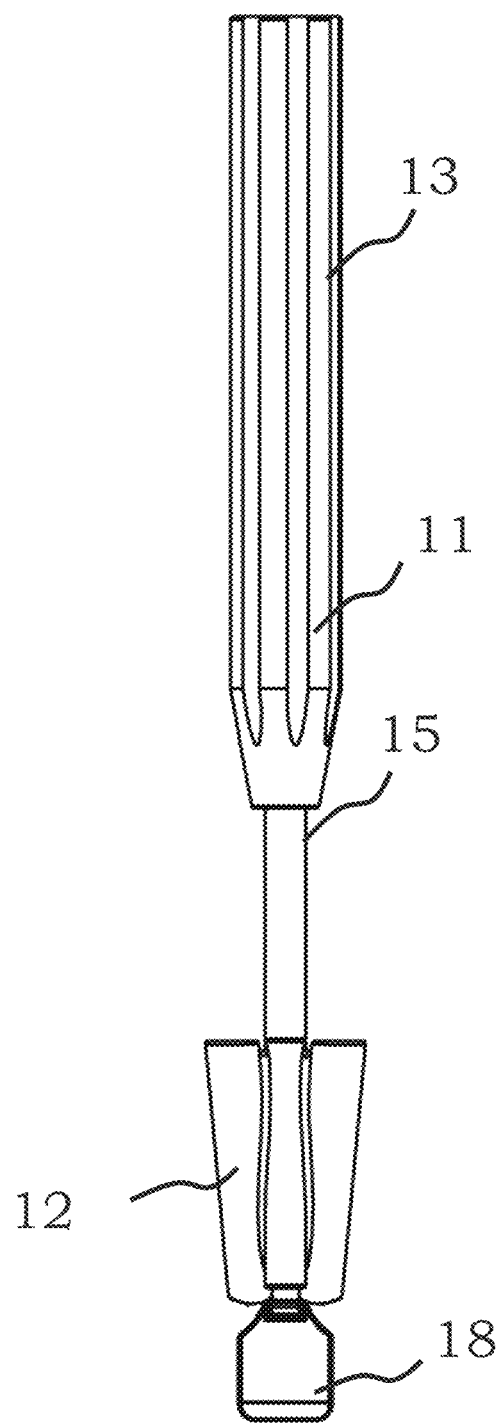
FIG. 2A illustrates a bottom view of an embodiment of the trial sizer.
Figure 2B:
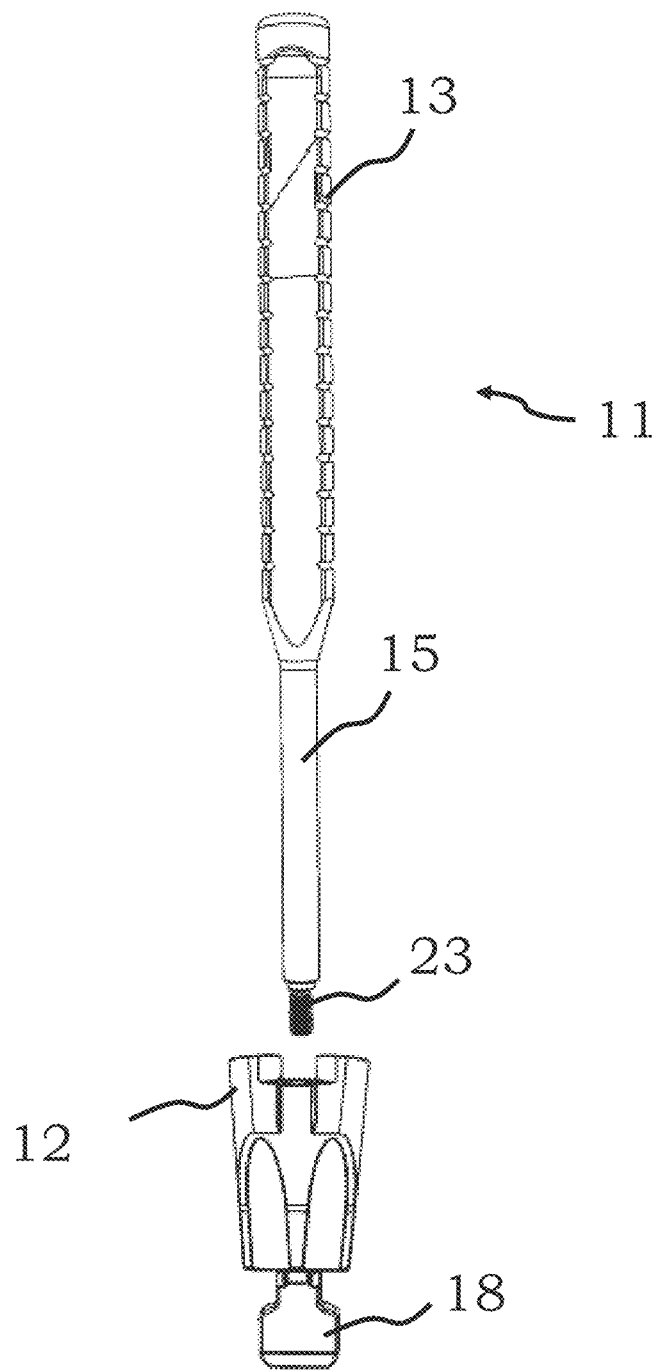
FIG. 2B is an exploded view of an embodiment of the trial sizer.

In some embodiments, handle section 11 is formed with or permanently joined to guide body 12 as depicted in FIG. 2A. In some embodiments, as shown in FIG. 2B, guide body 12 is detachable from handle section 11. The exemplary attachment mechanism depicted in FIG. 2A includes threaded section 23 disposed on the distal end of handle 11, which is configured to engage a complimentary thread receipt disposed in a proximal end of guide body 12. Guide body 12 may be temporarily attachable to handle section 11 via any method known to a person of ordinary skill in the art that would allow for quick and easy attachment/detachment during surgery. Non-limiting examples include complimentary threads, magnet connections, use of additional fasteners, detent and orifice connections, and latch and catch connections.

Figure 2C:
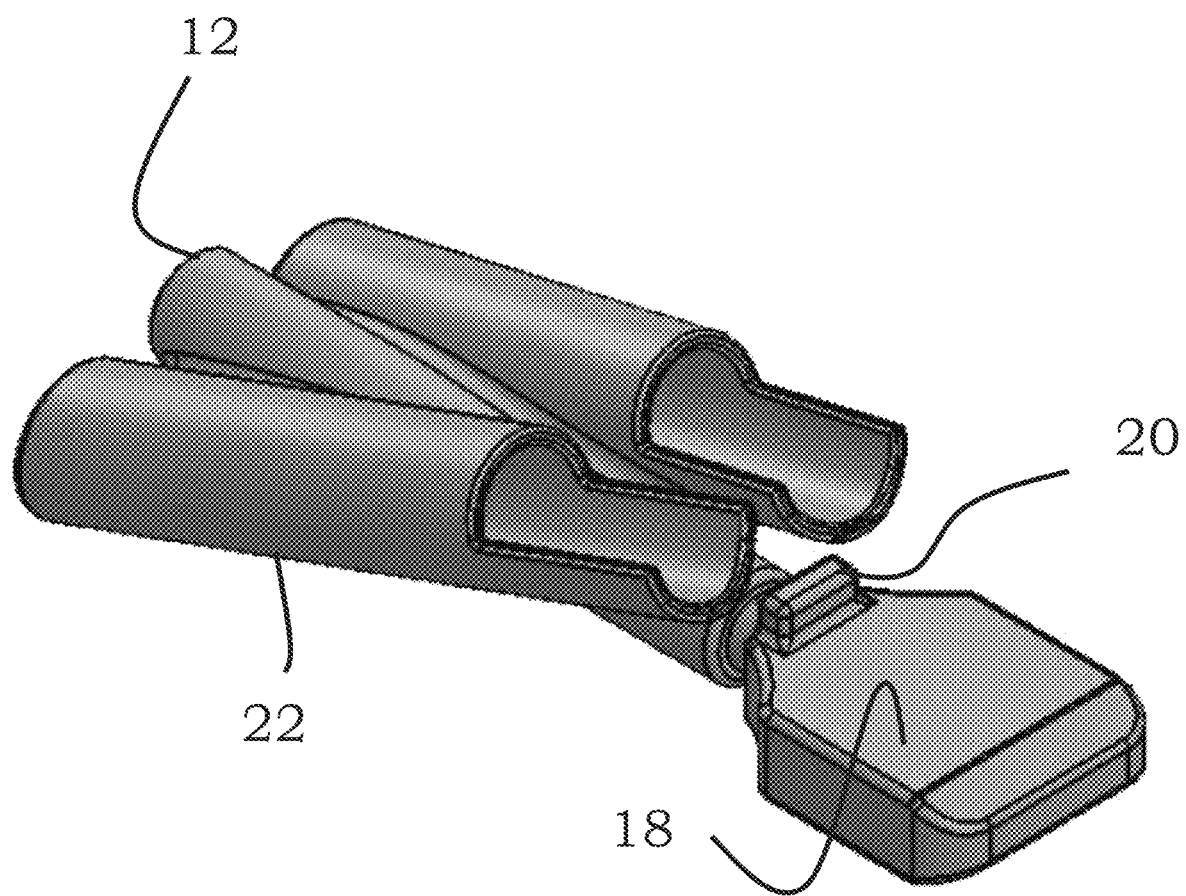
FIG. 2C is a close-up view of an embodiment of the spacer and guide body.
Figure 2D:
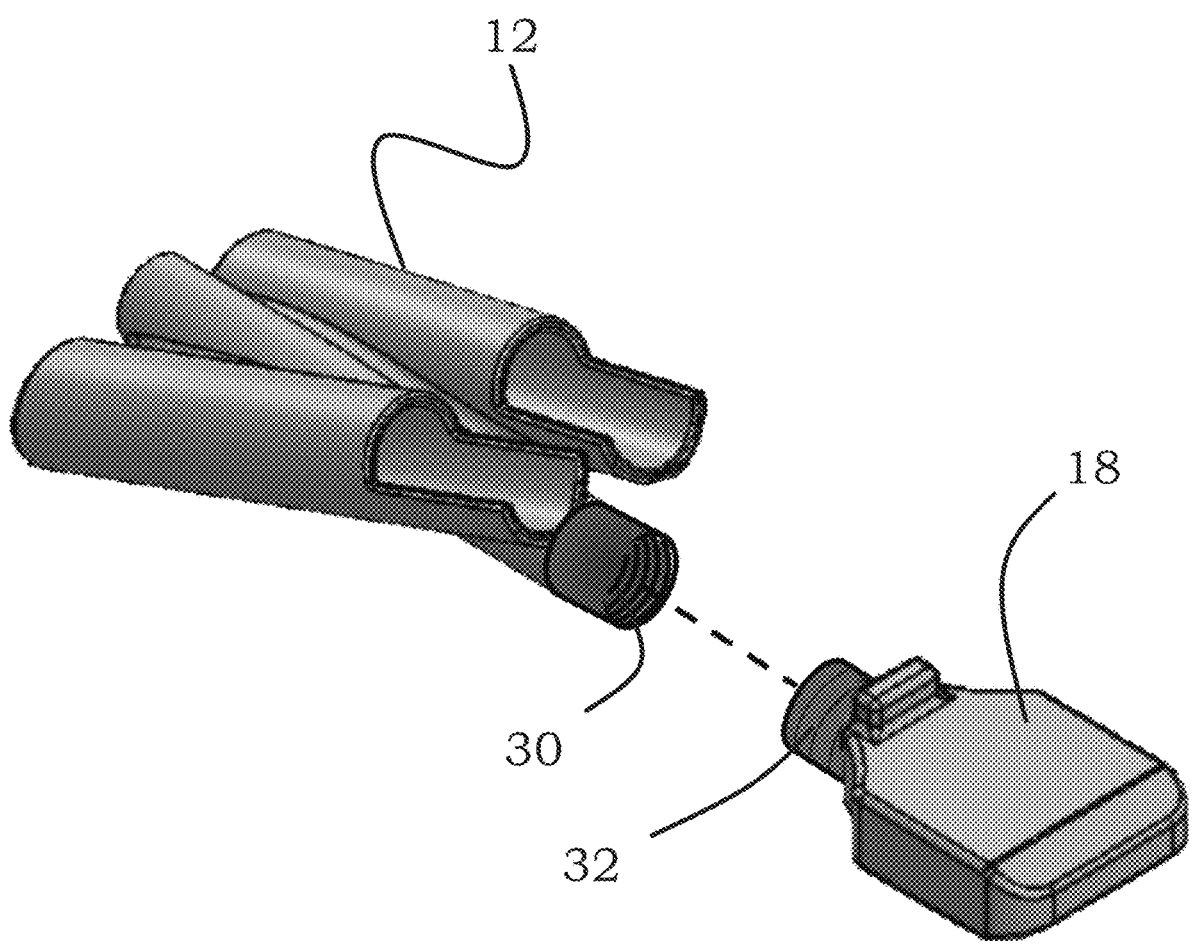
FIG. 2D is an exploded view of an embodiment of the spacer and guide body.

Spacer 18 can be formed with or permanently joined to guide body 12 as shown in FIG. 2C. In some embodiments, guide body 12 is detachable from spacer 18 as shown in FIG. 2D. As shown in FIG. 2D, guide body 12 includes thread receipt 30 configured to threadedly engage threaded section 32 on spacer 18. In some embodiments, guide body 12 includes threaded section 32 and thread receipt 30 is disposed in spacer 18.

In some embodiments, guide body 12 may be temporarily attachable to spacer 18 via any method known to a person of ordinary skill in the art. Non-limiting examples include, complimentary threads, magnet connections, use of additional fasteners, detent and orifice connections, and latch and catch connections.

In some embodiments, as depicted in FIGS. 3, guide body 12 is indirectly and temporarily attached to handle section 11. As shown, guide body 12 includes bore hole 9, which extends parallel to a longitudinal axis of guide body 12 and is configured to receive guide receiving section 17 of shaft 15. Guide receiving section 17 is located proximate to distal end 19 of shaft 15. In addition, guide receiving section 17 has a length roughly equal to the length of bore hole 9.

Guide receiving section 17 also includes a structural stop 21 to prevent guide body 12 from moving proximally along shaft 15 beyond an intended location. The depicted structural stop 21 is in the form of an annular stop created by the change in diameter of shaft 15. However, any other structural stop may be used as is known by a person of ordinary skill in the art. In addition, guide body 12 may be secured to guide receiving section 17 using attachment components known to a person of ordinary skill in the art.

Distal end 19 of shaft 15 further includes threaded section 23. As depicted in FIG. 3C, threaded section 23 extends distally beyond guide body 12 when guide body 12 is moved into contact with structural stop 21. Threaded section 23 is configured to engage complimentary thread 25 residing within aperture 27 in spacer 18. Because threaded section 23 extends beyond guide body 12, a user can easily attach/detach spacer 18 from the device. In some embodiments, threaded section 23 extends proximally from spacer 18 and threaded aperture 27 resides in shaft 15.

In some embodiments, spacer 18 may be temporarily attachable to handle 11 via any method known to a person of ordinary skill in the art that would allow for quick and easy attachment/detachment during surgery. Non-limiting examples include complimentary threads, magnet connections, use of additional fasteners, detent and orifice connections, and latch and catch connections.

The embodiments in FIGS. 2D and 3 provide the unique ability to more easily interchange spacers having different thicknesses for different vertebrae spacings. The embodiments in FIG. 3 provide the surgeon with the additional ability to remove guide body 12 to more easily visualize whether a particular spacer 18 with a predetermined thickness is appropriately sized to fit between a pair of vertebrae.

In some embodiments, the trial sizer is attachable to plate 100 and the surgeon has the option to remove spacer 18, attach plate 100, and use handle 11 to guide the insertion of plate 100. The surgeon may also remove guide body 12 prior to securing plate 100.

Figure 4A:
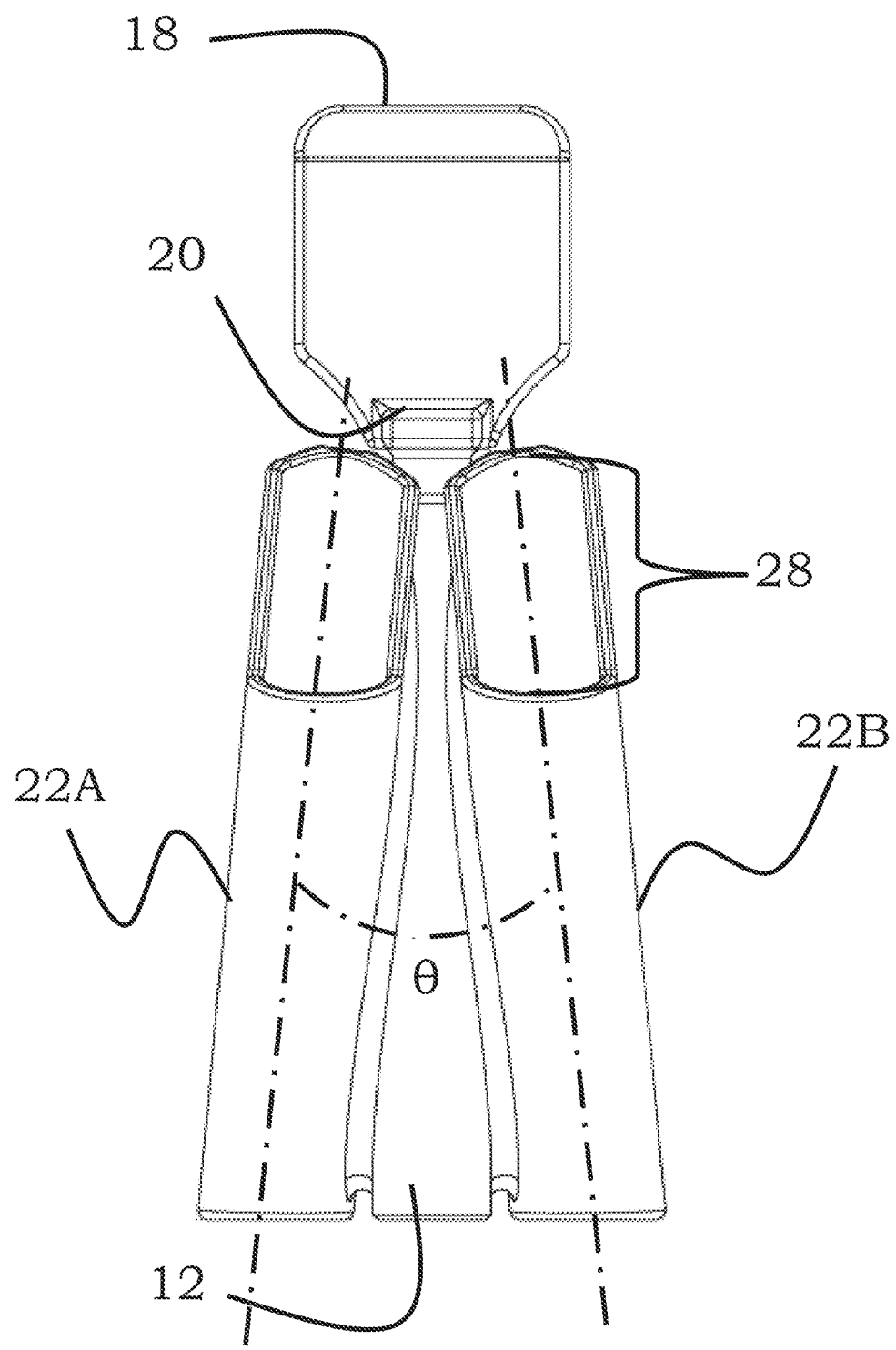
FIG. 4A is a close-up top view of an embodiment of the spacer and guide body.
Figure 4B:
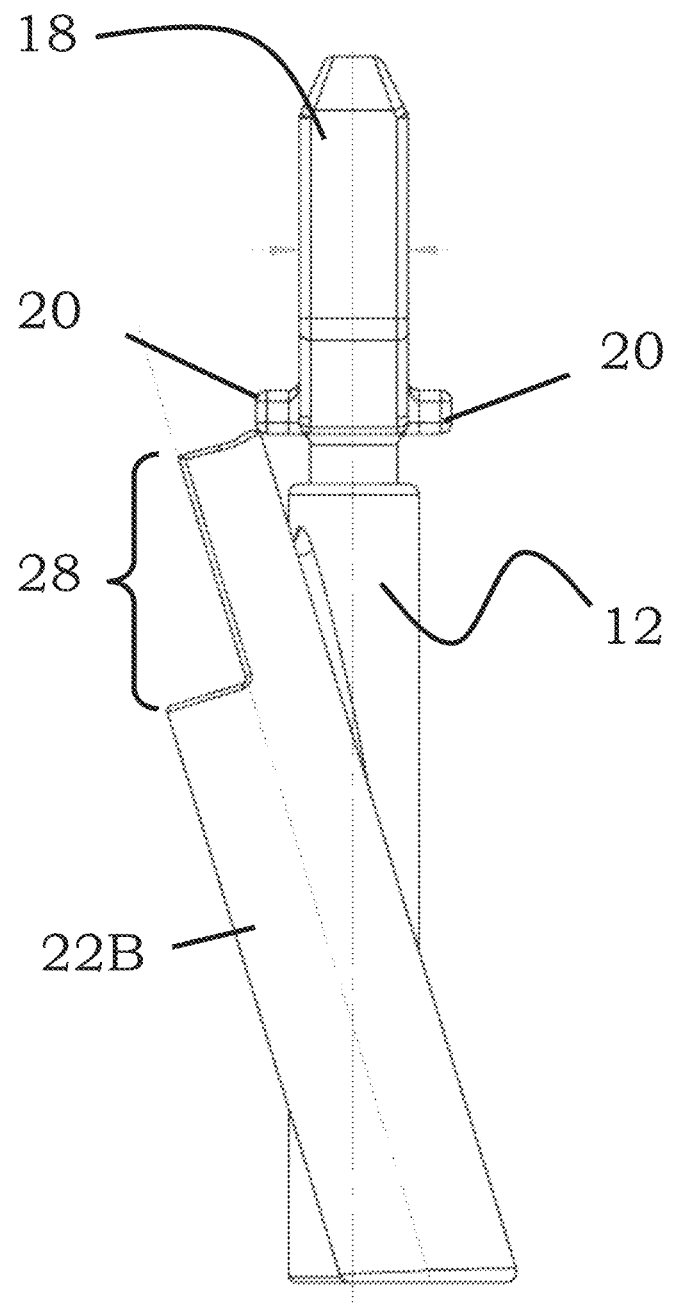
FIG. 4B is a close-up side view of an embodiment of the spacer and guide body.
Figure 4C:
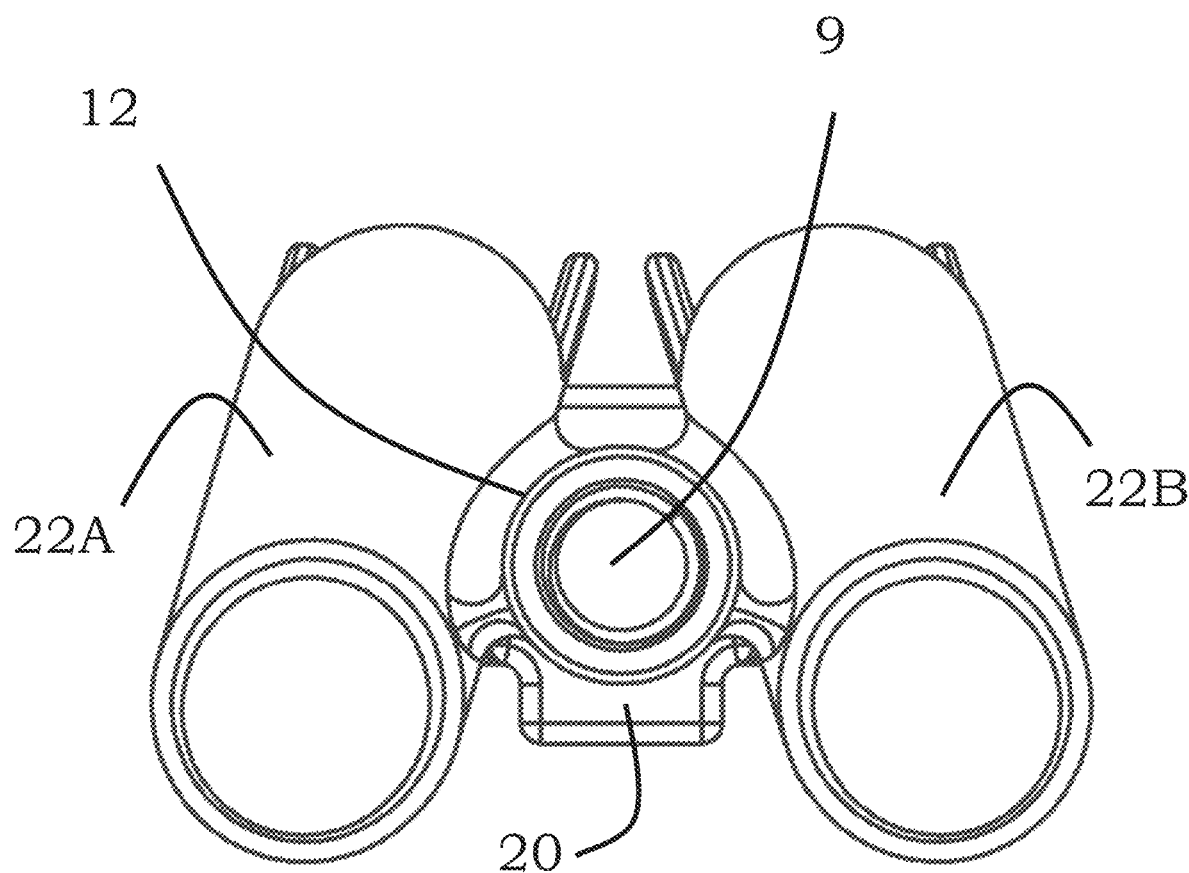
FIG. 4C is a close-up end view of an embodiment of the spacer and guide body.
Figure 4D:
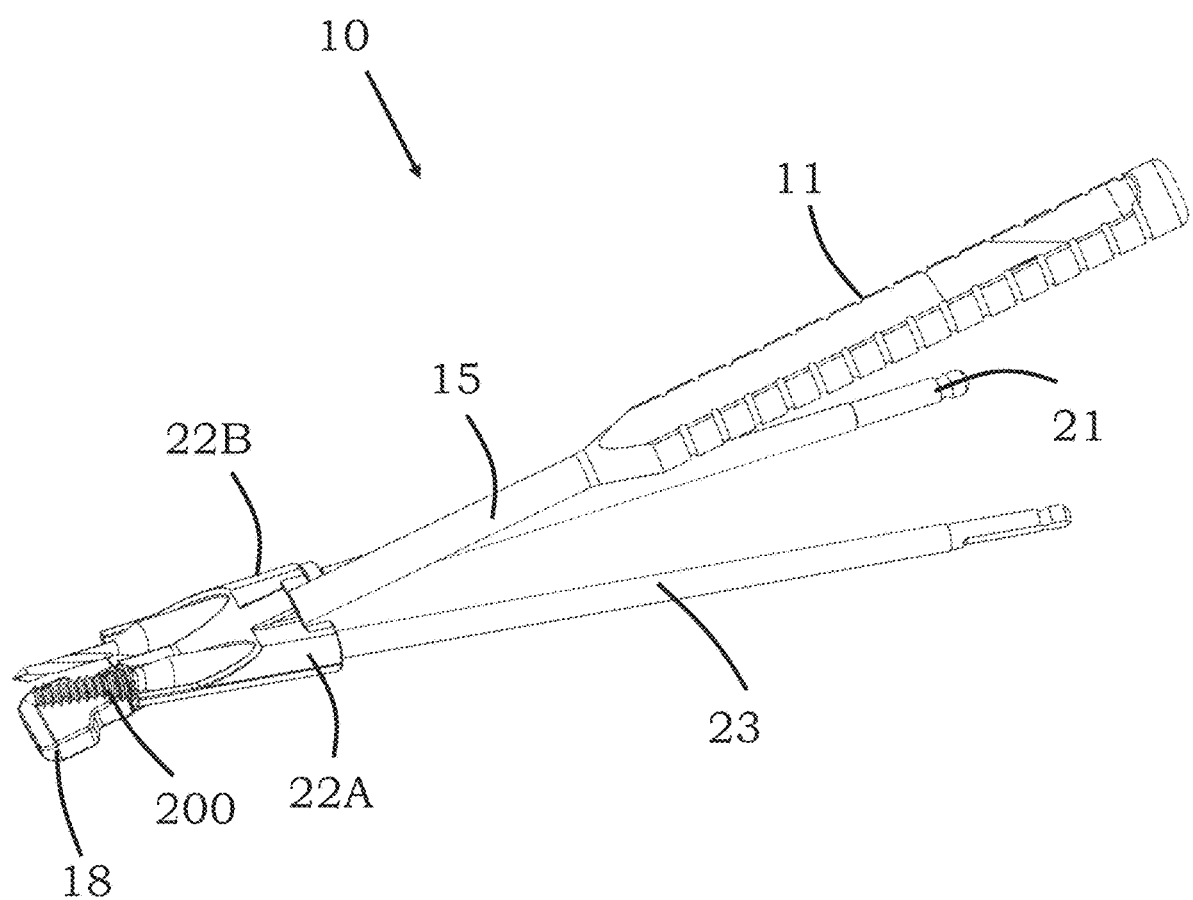
FIG. 4D is a perspective view of an embodiment of present invention with instruments disposed within the hollow instrument guides.
Figure 5:
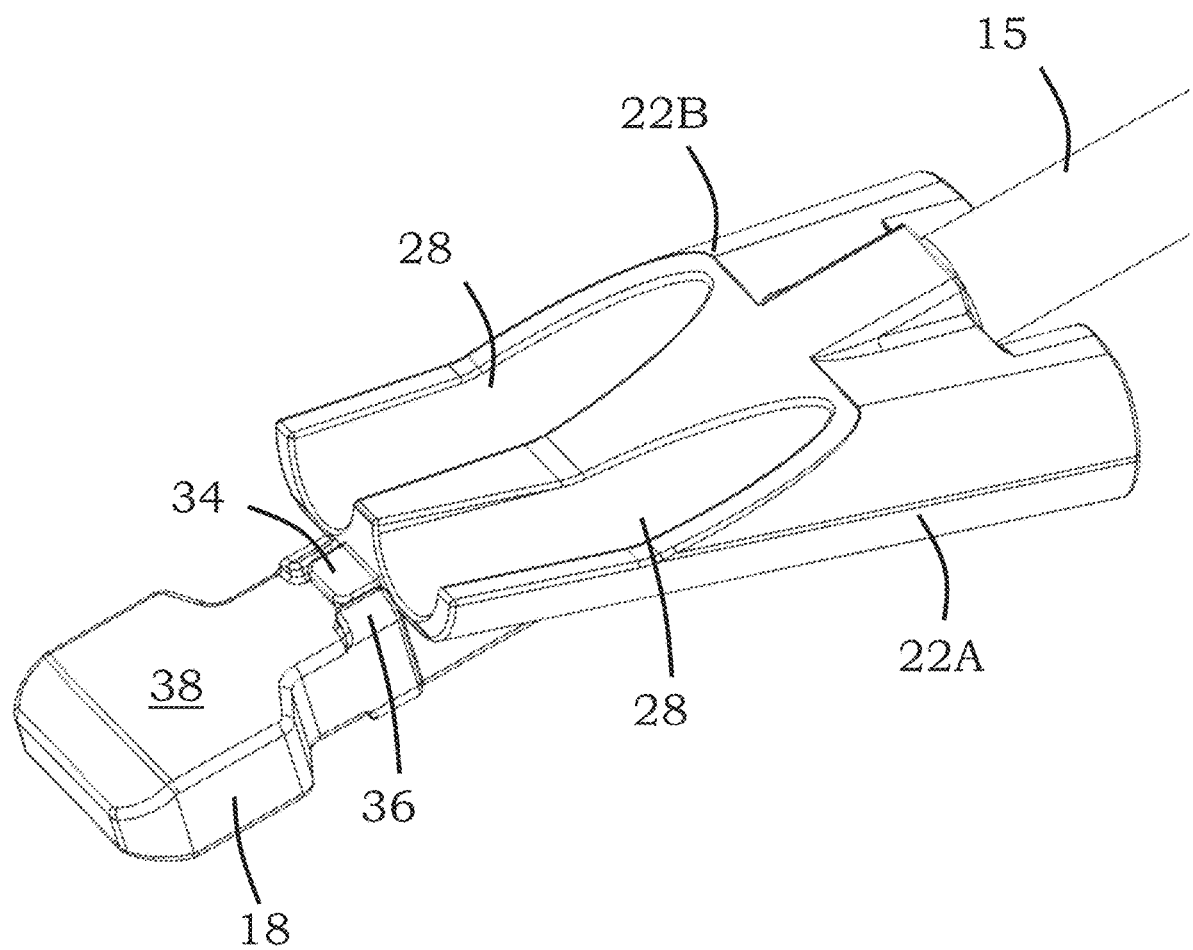
FIG. 5 is a close-up view perspective view of an embodiment of the spacer and guide body.
Figure 8:
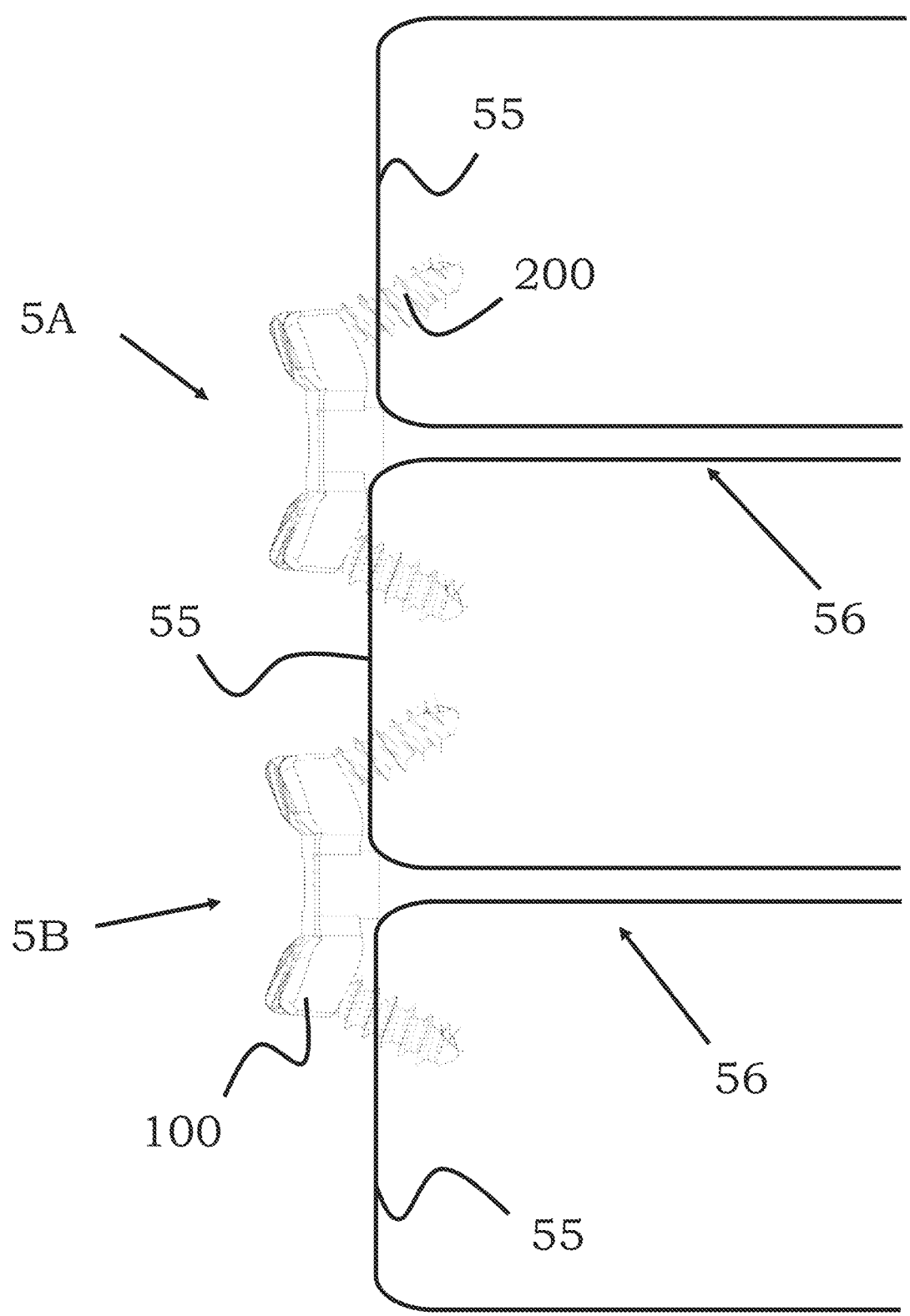
FIG. 8 illustrates an embodiment of the first assembly and the second assembly, each assembly secured to a patient's spine.

As most clearly depicted in FIG. 4-5, guide body 12 includes a pair of hollow instrument guides 22A and 22B. Each instrument guide 22 includes a hollow receipt extending in a distal direction at an angle offset from a longitudinal axis of shaft 15 and a longitudinal axis of spacer 18. The offset angle is designed to match the angle of plate 100 intended to be implanted. As a result, instrument guides 22 ensure that drilling instrument 21 produces a pilot hole in a proper orientation and in turn allows for the insertion of fastener 200 in the proper orientation, which can be seen in FIG. 8.

Each guide 22A and 22B may be coupled to guide body 12 in various geometric configurations and angles as deemed necessary for a particular surgery or patient. For example, pilot hole guides 22A and 22B may be angled at angle θ and arranged in an isosceles triangle configuration, shown best in FIG. 4A. In other words, guides 22A and 22B may be angled towards each other in a direction towards their distal ends. However, the configuration of pilot hole guides 22A and 22B are complementary to the orientation of apertures 108 of plate 100 (see FIGS. 6A, 6B, and 8).

Each hollow instrument guide 22 is configured to receive a surgical instrument. In some embodiments, each instrument guide 22 is sized to receive drilling instrument 21 and fastening instrument 23. In some embodiments, the internal diameter of each instrument guide 22 is sized to receive fastener 200, thereby enabling a surgeon to drill a pilot hole and insert fastener 200 without having to remove trial sizer 10. Generally, instrument guides 22 are tubular in shape but may be any shape, that allows for the instruments to pass through the hollow sections of instrument guides 22.

Some embodiments include each instrument guide 22 having cutaway windows 28 for viewing of the instruments during operation. For example, windows 28 allow a surgeon to see the drilling field as the drill bit passes through guide 22 and engages the bone. As a result, surgeons can confirm that they are not capturing soft tissue or engaging the wrong material when drilling the pilot holes or securing fastener 200.

Windows 28 also aids the surgeon to easily gauge the depth of fastener 200 to ensure that fastener 200 remains proud with respect to the surrounding bone. In some embodiments it is important to leave the first or first two fasteners 200 proud due to the unique manner in which fastener 200 and plate 100 interconnect, which is explained in greater detail below.

In an embodiment, guides 22 have a predetermined length, which in some embodiments may determine the depth at which the drill bit may be inserted into the bone. For example, when a drill bit is driven into the bone to a prescribed depth, the drill may contact the proximal end of pilot hole guide 22 preventing the drill bit from progressing deeper into the bone. In an embodiment, the drill bit may include a visual indicator, such as a painted line. This visual indicator allows a surgeon to visually determine the depth of the drill bit through cutaway portion 28. The prescribed depth at which the pilot hole is required to be drilled may be determined based on x-ray and/or magnetic resonance machine (MRI) imaging prior to or during surgery.

Trial sizer 10 further includes a vertebral spacer 18 attached to guide body 12 and/or handle 11. Spacer 18 is sized to be received within the space between a first and a second adjacent vertebral body (hereinafter "intervertebral space 56"). Placement of spacer 18 within intervertebral space 56 restricts the lateral, horizontal, and vertical movements of trial sizer 10. By preventing such movement, the correct alignment of trial sizer 10 in relation to the bone may be achieved.

In some embodiments, as best depicted in FIG. 4B, spacer 18 includes flange 20 to prevent spacer 18 from reaching a depth within the intervertebral space that may cause injury to the patient's spine. In an embodiment, one or more flanges 20 may protrude from spacer 18 in opposite vertical directions. Upon placement of spacer 18 into intervertebral space 56, at least a portion of flange 20 contacts at least a portion of one or both of the vertebral bodies. The contacting of flange 20 with one or more of the vertebral bodies provides a tactile and/or visual indication that trial sizer 10 is positioned at the prescribed depth within intervertebral space 56.

Spacer 18 is ideally formed having a rectangular prism shape, however, spacer 18 may include various geometries and sizes depending on an individual patient's spinal anatomy. For example, larger patients may require a thicker spacer 18 than patients with more petite body builds, such as younger patients. As depicted in FIG. 2D and FIGS. 3, when the need arises for a differently sized spacer 18, spacer 18 may be simply uncoupled from guide body 12 or threaded section 25 and replaced with a spacer of an appropriate size. The ability to interchange spacers 18 allows the surgeon and medical staff to tailor the trial sizer 10 based on each individual patient's anatomy, ensuring optimal placement of the pilot holes.

Figure 3A:
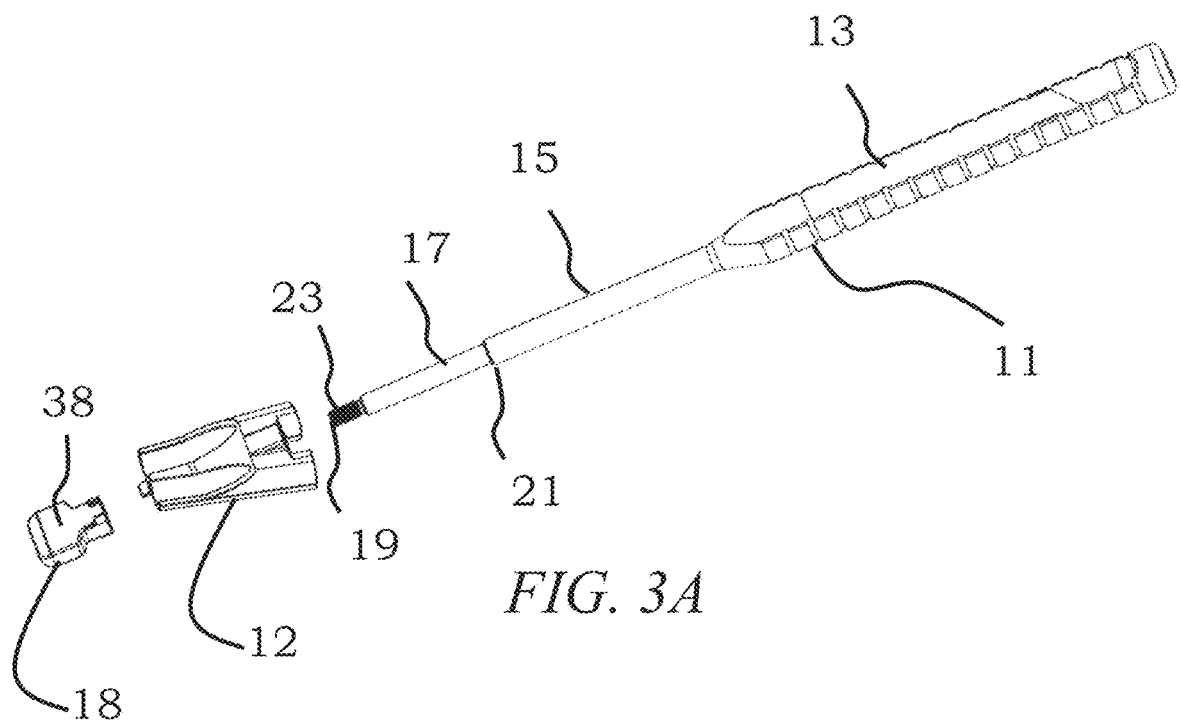
FIG. 3A is an exploded view of an embodiment of the present invention.
Figure 3B:
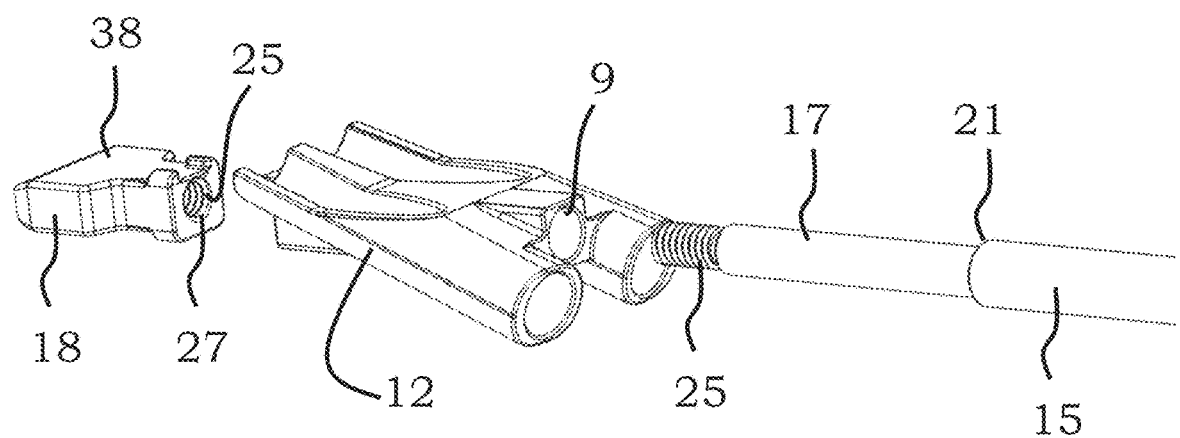
FIG. 3B is an exploded view of an embodiment of the present invention.
Figure 3C:
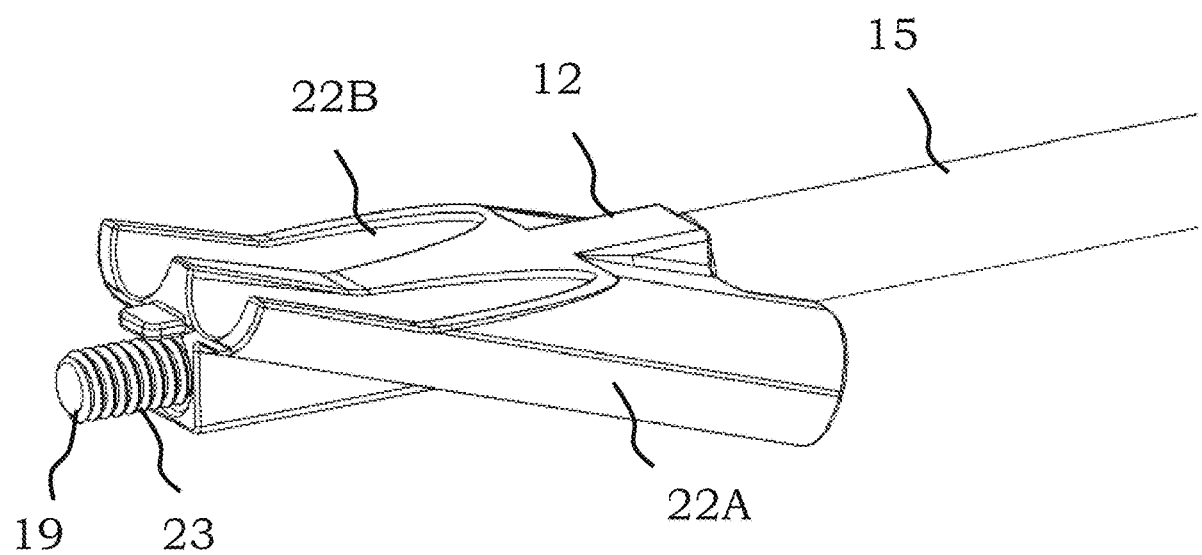
FIG. 3C is a perspective view of an embodiment of the present invention with the spacer removed.

In some embodiments, as best shown in FIGS. 3A-3B and 5, guide body 12 includes orientation tab 34, which is designed to be received by tab receipt 36 on spacer 18. The interconnection prevents spacer 18 from rotating relative to guide 12 when the two are brought into their respective operable positions.

In some embodiments, orientation tab 34 extends from spacer 18 and tab receipt 36 resides on guide body 12. Some embodiments include other alternative anti-rotation structures to prevent spacer 18 from rotating relative to guide 12 when the two are brought into their respective operable positions.

Some embodiments of spacer 18 include operational surface 38, which is intended to be the surface closer to the distal ends of guides 22. Some embodiments include visual and/or tactile indicators to assist user in identifying the operational side. Some embodiments include tab receipt 26 residing on operational surface 38 of spacer 18.

Some embodiments include a set of spacers of different thicknesses with tab receipts 36 on a single surface of each spacer 18. In addition, each spacer 18 includes aperture 27 located at the same distance from operational surface 38. Thus, regardless of how thick a spacer is, the pilot holes will always be drilled at the same distance from operational surface 38 of spacer 18.

Some embodiments include the center of aperture 27 being 2.5 mm from operational surface 38. Some embodiments include the center of aperture 27 being 2-3 mm from operational surface 38. Some embodiments include the center of aperture 27 being 1.5-3.5 mm from operational surface 38.

Once the surgeon has identified the proper spacer 18 based on the size of intervertebral space 56 and the thickness of spacer 18, the surgeon can attach the proper spacer 18 to handle 11. As depicted in FIG. 10, the surgeon can then insert spacer 18 into intervertebral space 56 and use guides 22 to align surgical drill 21 and subsequently drill the pilot holes at the correct angle within the bone. Guides 22 are in substantially the same orientation and angle as apertures 108 of plate 100, such that when the pilot hole is drilled, fasteners 200 (see FIG. 7) can be secured within a patient's bone in the correct position and orientation to ensure that fasteners 200 properly align with and thereby engage apertures 108 of plate 100.

Figure 6A:
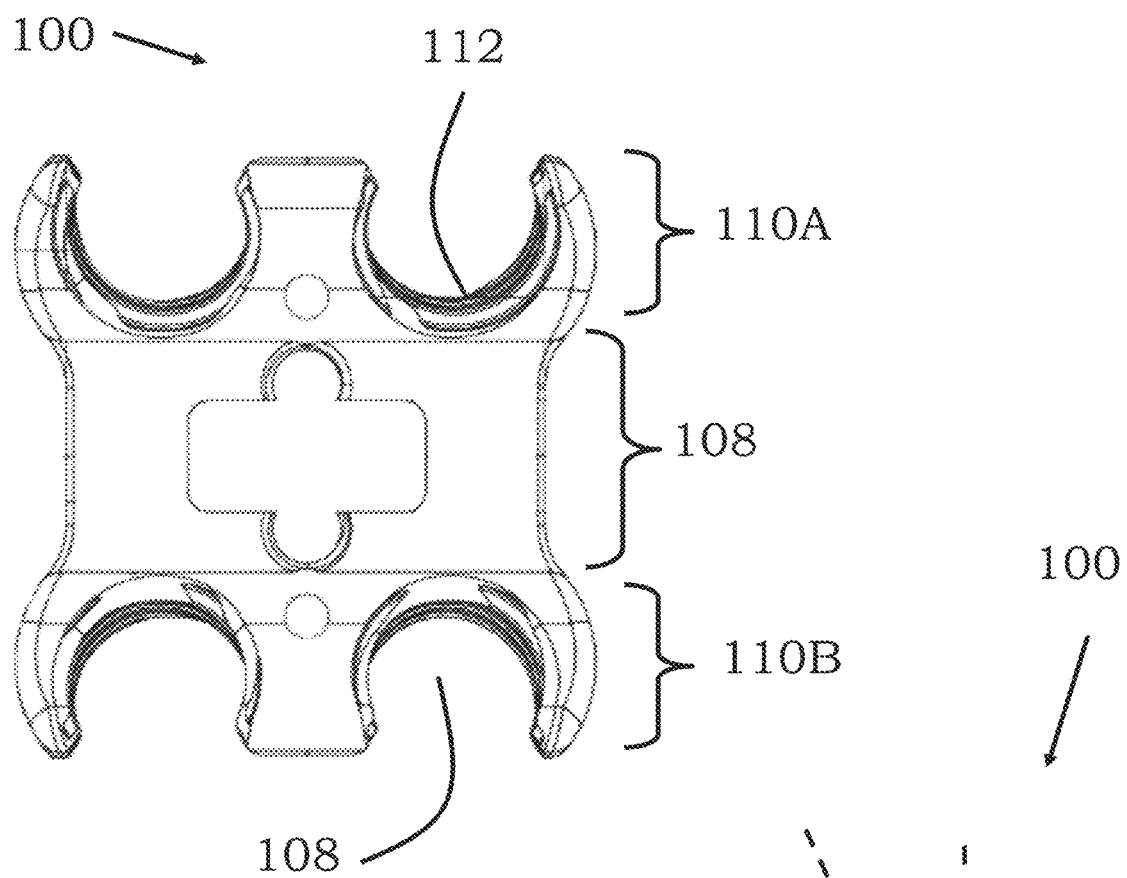
FIG. 6A illustrates a top view of an embodiment of the first interacting element, in the form of an implantable plate.
Figure 6B:
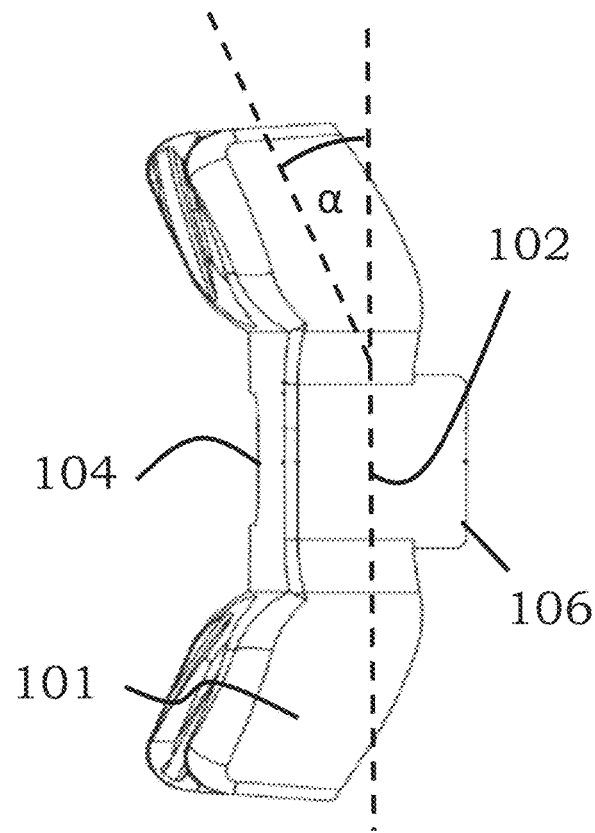
FIG. 6B illustrates a side view of an embodiment of the first interacting element.
Figure 6C:
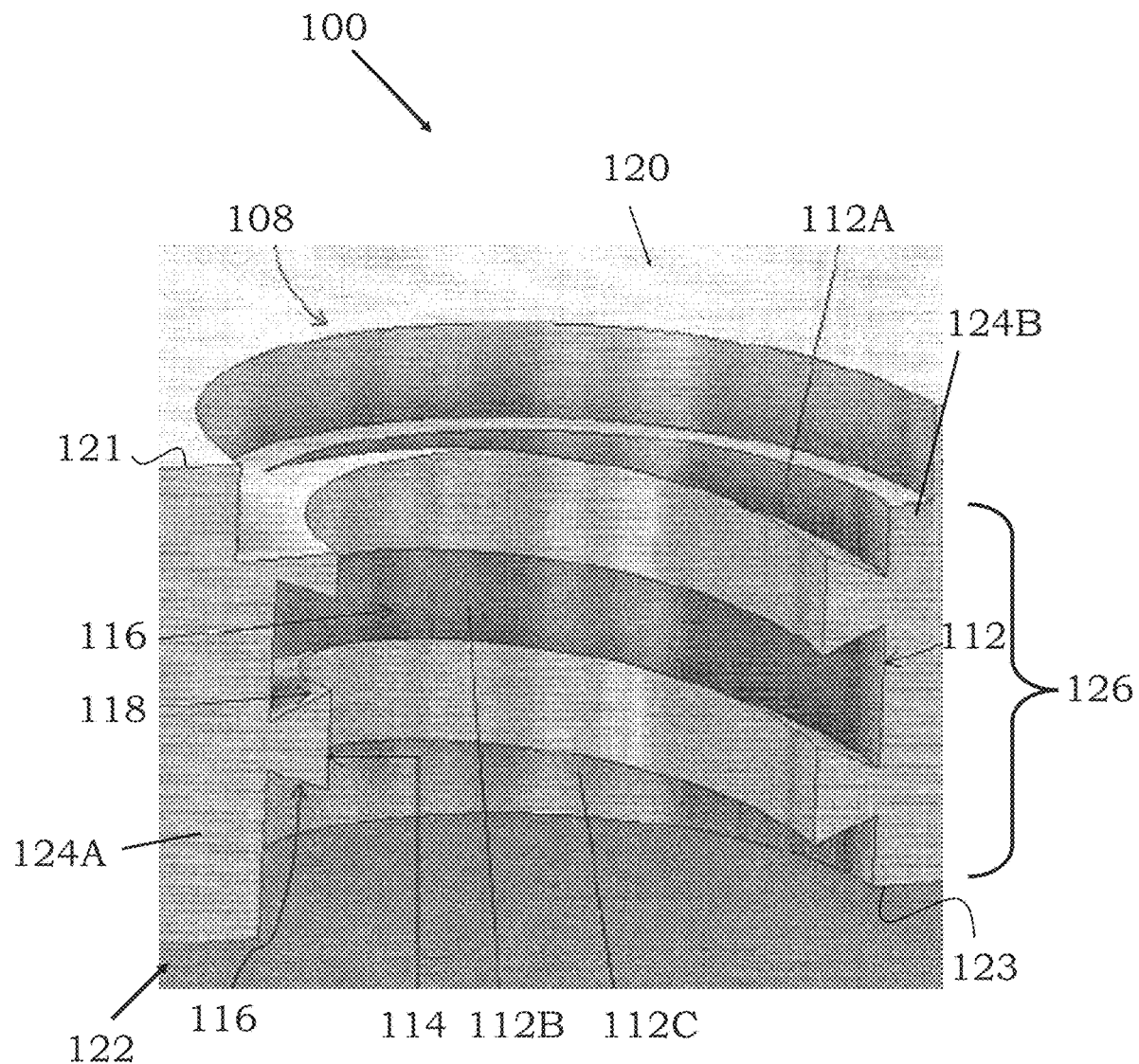
FIG. 6C illustrates a cutaway view of an embodiment of the aperture depicting the thread receiving elements.

Some embodiments of trial sizer 10 are designed for surgical procedures involving unique implantable interacting elements. FIGS. 6A-6C illustrate a first implantable interacting element in the form of plate 100 according to an embodiment of the invention. Plate 100 includes upper plate body surface 104 and lower plate body surface 106. Plate 100 also includes body portion 108 residing in plane 102. A pair of fastening cantilevers 110A and 110B are bent out of plane 102 at angle α. Each fastening cantilever 110 is positioned on opposite sides of body portion 106 and includes one or more apertures 108 disposed therein. Fastening cantilevers 110 are disposed at angle α in relation to plate 102 to ensure that when fasteners 200 (see FIG. 7) engage thread receiving elements 112 of apertures 108, fasteners 200 are angled away from an edge of the bone, thereby reducing the risk of the bone splintering.

In an embodiment angle α is between 5-30 degrees. When α is greater than 5 degrees, fastener 200 is unlikely to splinter the bone and when α is less than 30 degrees, fastener 200 is unlikely to contact any fasteners 200 secured to an adjacently located plate 100 secured on an opposite end of the bone. In an embodiment, angle α is between 12-22 degrees. When α is between 12 and 22 degrees, there is even less chance of splintering the bone or fasteners 200 from first assembly 5A contacting fasteners 200 from second assembly 5B (see FIG. 8). In an embodiment, angle α is 17 degrees. When fastener 200 engages the bone at about 17 degrees, the chance of splintering the bone or contacting other fasteners 200 from adjacent assemblies 5B is reduced to a minimum.

In an embodiment, apertures 108 are incomplete/semi-circular apertures in which the incomplete section of the circumference is an opening in lateral surface 101 of plate 100. When the circumferential opening is located in lateral surface 101 of plate 100, the size of plate 100 is inherently reduced. In addition, the circumferential opening in lateral surface 101 of plate 100 enables a user to first secure fastener 200 and then position the plate 100 in a lateral manner, such that the circumferential opening receives the already secure fastener 200. Fastener 200 can then be further rotated so that thread component 204A (see FIG. 7) engages thread receiving element 112 in plate 100, thereby setting the location of plate 100 prior to drilling additional pilot holes or screwing additional fasteners 200 into the bone to further engage plate 100.

In an embodiment, apertures 108 may be any semi-circular shape such that the lateral opening in the circumference is greater than a diameter of at least a portion of fastener 200 (see FIG. 7) to ensure that the lateral opening can receive fastener 200 when fastener 200 is already secured in the bone. In an embodiment, apertures 108 may have any circumferential length that allows thread receiving element 112 of plate 100 to engage with thread component 204 of fastener 200, thereby securing fastener 200 to plate 100.

As depicted in FIG. 6C, apertures 108 may include thread receiving element 112 having outer receiving surface 114, upper receiving surface 116, inner receiving surface 116, and lower receiving surface 118. In certain embodiments, any surface, including outer receiving surface 114, upper receiving surface 116, inner receiving surface 116, and lower receiving surface 118 may be linear or curved.

Thread receiving element 112 is configured to receive thread component 204 on fastener 200. In embodiments in which thread component 204 includes multiple helical turns, thread receiving element 112 may include more than one thread receiving elements 112, such as first thread receiving element 112A, second thread receiving element 112B, and third thread receiving element 112C. Any number of thread receiving elements 112 are contemplated.

In the embodiment illustrated in FIG. 6C, first thread receiving element 112A is positioned closest to first surface 120 of plate 100. Third thread receiving element 112C is positioned closest to second surface 122 of plate 100. Second thread receiving element 112B is positioned between first thread receiving element 112A and third thread receiving element 112C. In an embodiment, thread receiving elements 112 may be tapered in size such that the respective portion of thread component 204 may be secured in position.

In certain embodiments, one or more thread receiving elements 112 are positioned along lateral surface 124 of plate 100, such that only certain portions of thread component 204 are enclosed within thread receiving element 112. One or more thread receiving elements 112 may be flanked by first lateral surface 124A and second lateral surface 124B of plate 100. Lateral surfaces 124A and 124B meet with first surface 120 at upper edge 121 and second surface 122 at lower edge 123. The distance between first surface 120 and second surface 122 results in thickness 126. The thickness 126 influences the number of thread receiving elements 112, however, at least one thread element 112 is disposed in plate 100.

In an embodiment, thread receiving element 112 may receive thread component 204. Thread component 204 may be shaped in multiple helical turns, for example, turns that start at or near second surface 122 of plate 100 and end at or near top surface 120 of plate 100. Alternatively, thread receiving element 112 may receive thread component 204 shaped in a single helical turn or less than a full helical turn. For purposes of this application, a "full helical turn" is a complete 360-degree rotation around a cylindrical axis. (Similarly, if the rotation was in a flat plane instead of a cylindrical axis, the shape would be a circle, not a helix.)

FIG. 7 illustrates an embodiment of a second implantable interacting element in the form of fastener 200. Fastener 200 includes first body component 202A and second body component 202B. First body component 202A includes first thread component 204A configured to interface with plate 100. Second body component 202B includes second thread component 204B configured to interface with the bone. Thread components 204A and 204B are positioned relative to body components 202A and 202B respectfully, such that upon rotating fastener 200, thread component 204A is received by thread receiving element 112 of plate 100 and thread component 204B is disposed through a surface of the bone. As shown in this embodiment, cutting flute element 206 may be provided to facilitate a self-tapping capability.

In an embodiment, second body component 202B, including second thread component 204B, is configured to have a smaller cross-section diameter than the cross-section diameter of first body component 202A, including first thread component 204B. First body component 202A includes proximal end 208 and distal end 210 positioned adjacent to second body component 202B. Such embodiments may be configured in which first body component 202A is configured to interact with thread receiving element 112 of plate 100 and second body component 202B is configured to interact with the bone.

In an embodiment, first thread component 204A may be continuous with or connected to second thread component 204B via a thread-thread connector (not shown). The thread-thread connector may have a tapered shape. In other embodiments, first thread component 204A and second thread component 204B are completely integrated and have no connection.

Figure 7A:
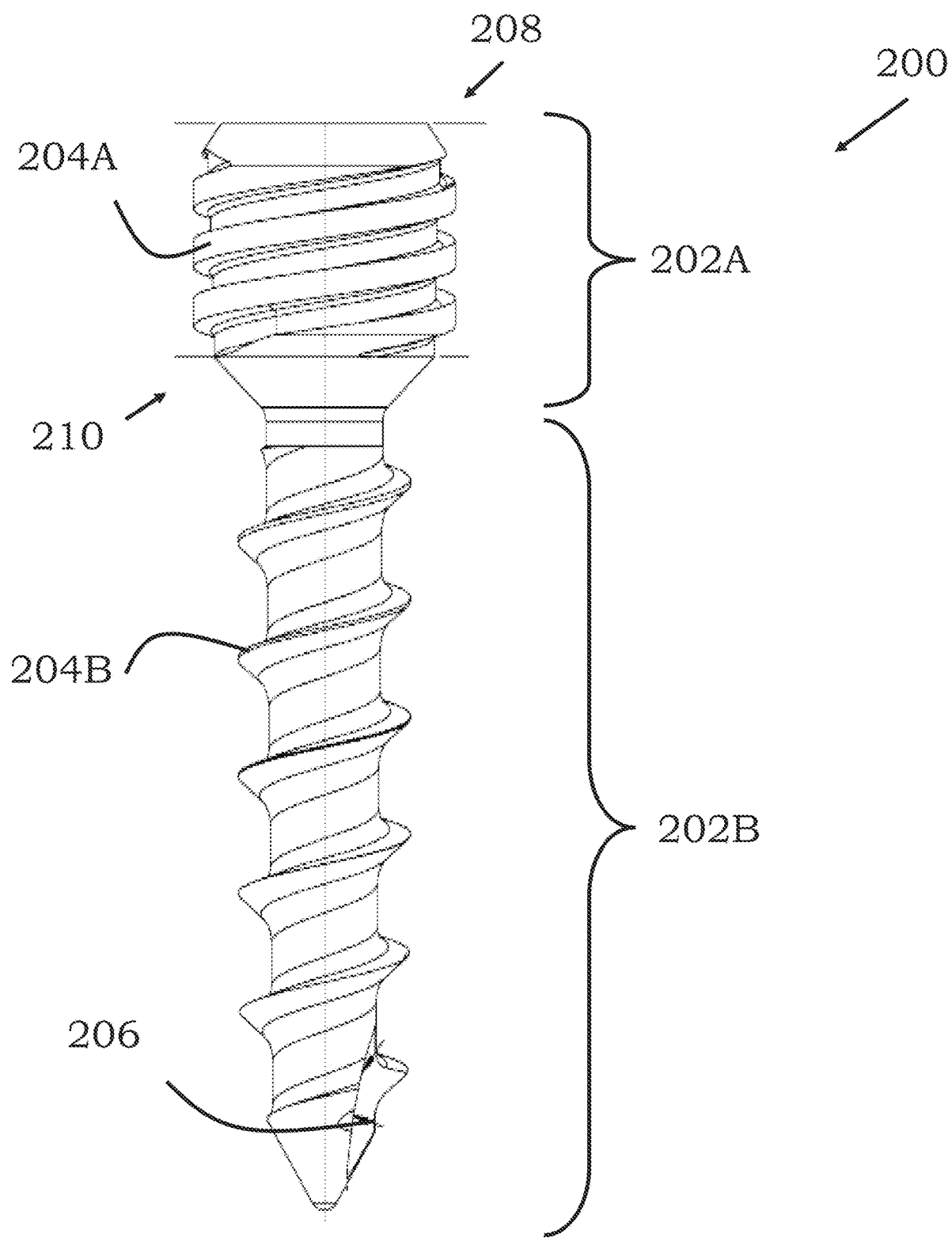
FIG. 7A illustrates an embodiment of the second interacting element, in the form of a fastener.
Figure 7B:
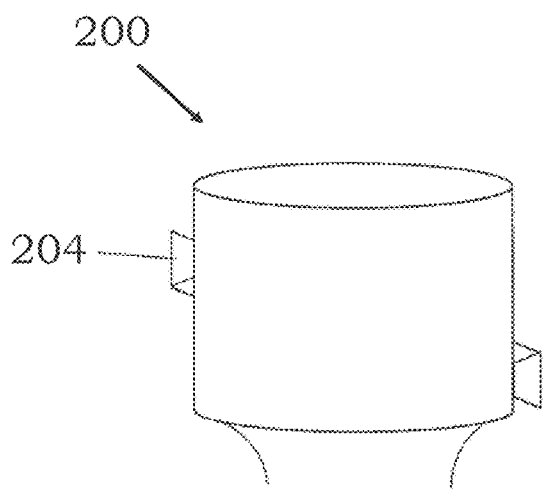
FIG. 7B illustrates an embodiment of the fastener having a thread component including only a partial helical turn.
Figure 7C:
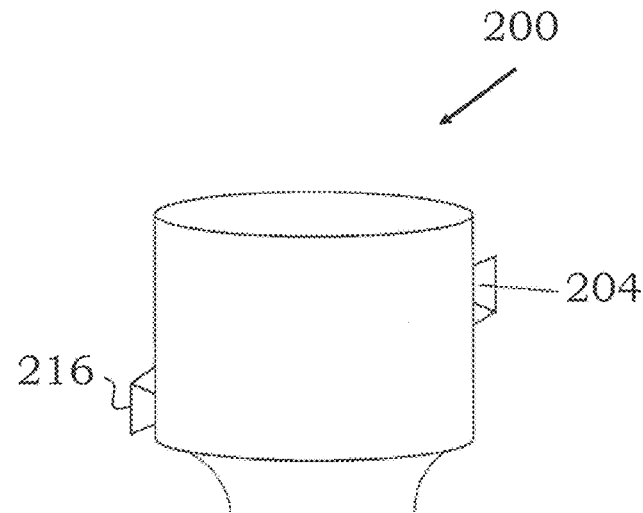
FIG. 7C illustrates an embodiment of the fastener having a thread component including only a partial helical turn.
Figure 7D:
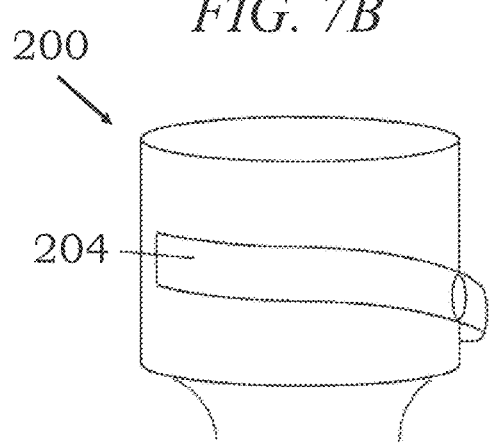
FIG. 7D illustrates an embodiment of the fastener having a thread component including only a partial helical turn.
Figure 7E:
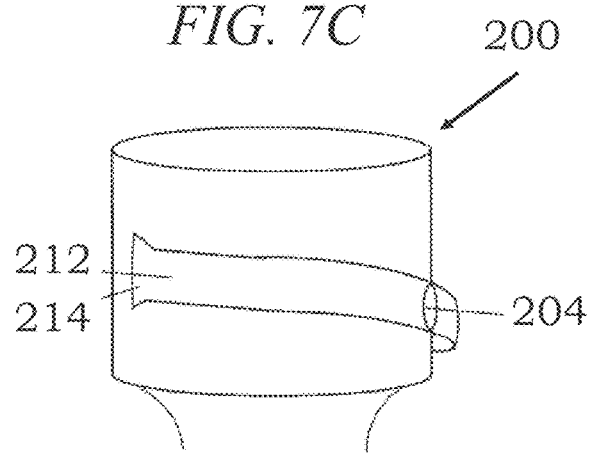
FIG. 7E illustrates an embodiment of the fastener having a thread component including only a partial turn of a helix and the thread component includes a stop element.

In an embodiment, as shown in FIGS. 7B and 7C, the helical shape of thread component 204 may be left-handed or right-handed and may be a full or partial helical shape. In certain embodiments, the entire fastener 200 is a single unit formed by, for example, injection molding. In other embodiments, certain portions of fastener 200 are formed separately from thread component 204 and then the pieces are subsequently attached together.

Thread component 204 may also include origination end 212. Origination end 212 may be enlarged with respect to the remaining portion of thread component 204 to form stop 214. As such origination end 212 prevents thread component 204 from further moving into thread receiving element 112 of plate 100.

Figure 7F:
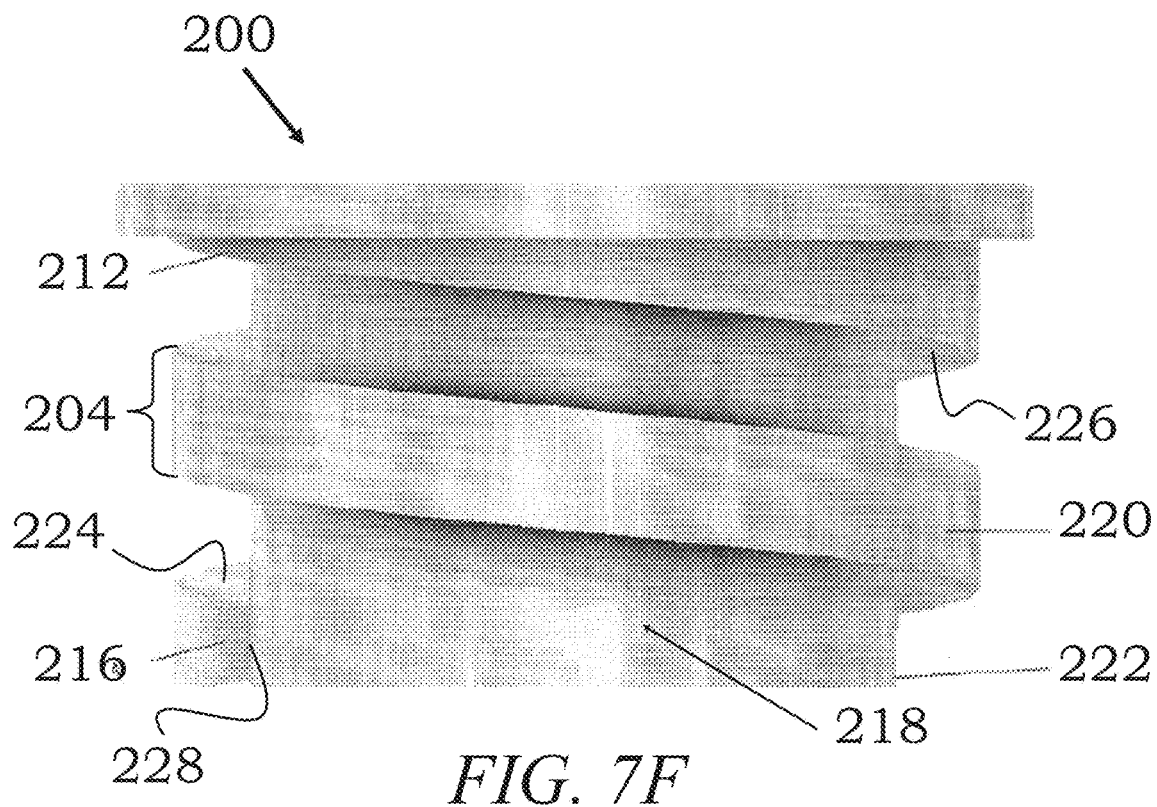
FIG. 7F illustrates an embodiment of the fastener having thread component positioned relative to the fastener body.
Figure 7G:
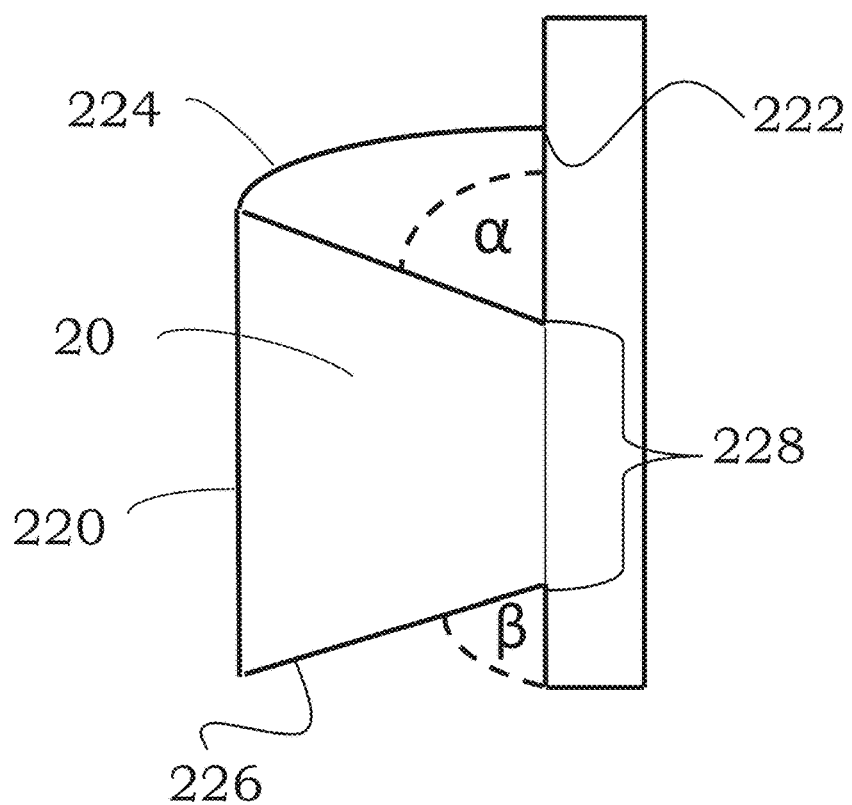
FIG. 7G illustrates an embodiment of the fastener depicting a close of view of the thread component.

An embodiment of fastener 200, as depicted in FIGS. 7F-7G, further includes thread termination end 216. Thread termination end 216 is shaped to be received within thread receiving element 112. Thus, thread component 204 can be positioned relative to fastener body 218, such that upon rotating fastener 200, thread component 204 is received by thread receiving element 112 of plate 100.

In certain embodiments, the size of thread components 204 is static throughout the entire thread component 204. In other embodiments, thread base surface 228 and outer fastener body surface 222 is smaller in length near thread termination end 216 and larger in length near thread origination end 212. The length of thread component 220 may increase continuously (e.g., taper continuously) throughout the length of thread component 220 or may increase more sharply only near thread origination end 212. In an embodiment, at least a portion of upper thread surface 224 and/or lower thread surface 226 is wider than thread base surface 228, which is generally continuous with outer fastener body surface 222. Such embodiments are configured to permit locking of thread component 204 into thread receiving element 112 when the larger portion of thread component 204 meets with or is compressed into thread receiving element 112.

Thread component 204 may be inversely complementary to the size and shape of thread receiving element 112 of plate 100, such that the thread component 204 is secure within thread receiving element 112 and may not be disposed laterally away from plate 100. This relationship is best depicted in FIGS. 7F and 7G. In the depicted embodiment thread component 204 includes outer thread surface 220 that may be generally parallel to outer fastener body surface 222. In addition, thread component 204 includes at least upper thread surface 224 and lower thread surface 226 configured to adjoin outer thread surface 220 to outer fastener body surface 222. In an embodiment, the angle α between upper thread surface 224 and outer fastener body surface 222 is between 45 and 90 degrees. In an embodiment, the angle β between lower thread surface 226 is between 45 and 90 degrees.

Figure 9:
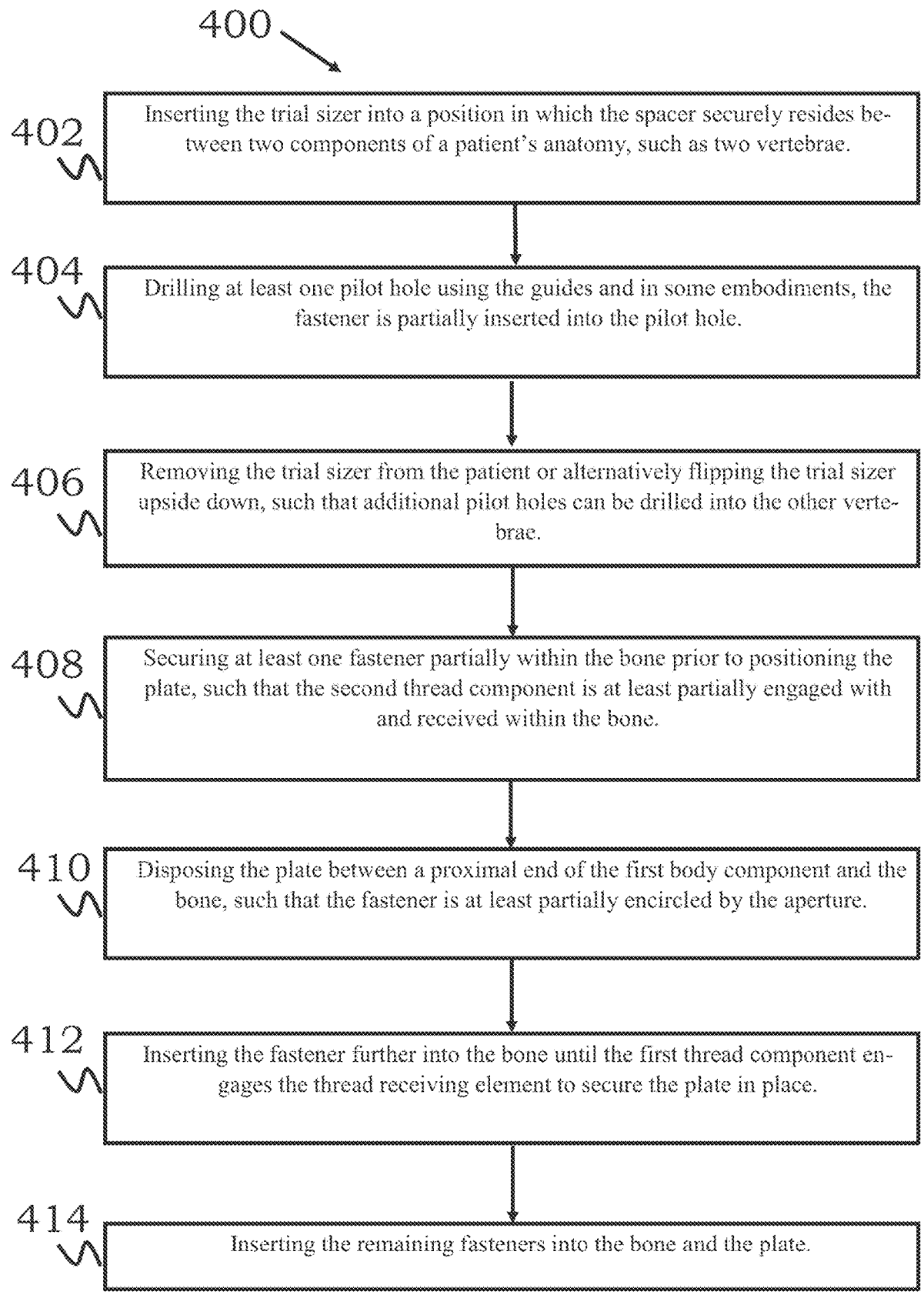
FIG. 9 is a flow chart of an embodiment of the novel method of securing an implant to a bone.

An embodiment of the present invention includes a novel method 400 for securing an implant to a bone, which is exemplified in FIG. 9. In step 402, an embodiment of trial sizer 10 is inserted into a position in which spacer 18 securely resides between two components of a patient's anatomy, such as two vertebrae. FIG. 10 illustrates this positioning. At step 404, at least one pilot hole can be drilled using guides 22 and drilling instrument 21. Preferably two holes are drilled, one from each hollow instrument guide 22.

Drilling instrument 21 is then removed and preferably, fasteners 200 are partially secured in both pilot holes. At least one fastener 200 is partially secured within bone 55 prior to positioning plate 100, such that second thread component 204B is at least partially engaged with and received within bone 55 at step 408.

Then at step 406, trial sizer 10 can be removed from the patient and/or alternatively flipped upside down and additional pilot holes can be drilled into the other vertebrae. At step 410, plate 100 is then slidably disposed between proximal end 208 of fastener(s) 200 and bone 55, such that fastener(s) 200 are at least partially encircled by aperture(s) 108. Next, at step 412, once plate 100 is in position, fastener(s) 200 are further threaded into bone 55 until first thread component(s) 204A engage thread receiving elements 112 to secure plate 100 in place. Lastly, step 414, the remaining fasteners 200 can then be secured in bone 55 and to plate 100.

While the disclosure is susceptible to various modifications and alternative forms, specific exemplary embodiments of the present invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A kit configured for drilling one or more pilot holes and inserting fasteners into a patient's vertebrae prior to inserting or securing a plate to the patient's vertebrae, comprising:
   a trial sizer having a handle and a guide body;
   a plurality of spacers temporarily attachable to a distal end of the trial sizer,
   wherein each of the plurality of spacers includes a first surface, a second surface, and a longitudinal axis extending between a proximal end and a distal end of the respective spacer;
   the trial sizer further including:
      a gripping section proximate to a proximal end of the trial sizer;
      the distal end of the trial sizer configured to engage each of the plurality of spacers; and
      the guide body located between the distal end and the proximal end of the trial sizer;
   the guide body further including a hollow instrument guide with a bore hole extending from a proximal end to a distal end of the hollow instrument guide and a longitudinal axis extending therebetween;

each of the plurality of spacers having a different thickness extending between respective ones of the first and second surfaces of each spacer;

each of the plurality of spacers configured to engage the trial sizer such that the respective first surface of each of the plurality of spacers is at a same relative distance and orientation from the distal end of the hollow instrument guide when the respective one of the plurality of spacers is engaged with the trial sizer, thereby causing the pilot holes to be drilled at drilling locations on one of the vertebrae independent of the thickness of the respective one of the plurality of spacers;

whereby the respective one of the plurality of spacers is configured to be inserted between two of the patient's vertebrae and the guide body is configured to guide a user to the drilling locations on the one of the vertebrae.

2. The kit of claim 1, wherein the bore hole in the hollow instrument guide has a diameter sized to receive one of the fasteners intended for insertion into the patient's vertebrae, whereby the fastener is configured to be inserted through the bore hole in the hollow instrument guide to secure the fastener in the patient's vertebrae without having to first remove the trial sizer from the patient.

3. The kit of claim 1, wherein the each of the plurality of spacers is detachably connected to the trial sizer.

4. The kit of claim 1, wherein the guide body can be removed from a rest of the trial sizer.

5. The kit of claim 1, wherein the hollow instrument guide is one of a pair of hollow instrument guides angled towards each other moving in a distal direction.

6. A kit for drilling one or more pilot holes and inserting fasteners into a patient's vertebrae, comprising:
   a trial sizer having a handle and a universal guide body;
   a plurality of spacers temporarily attachable to a distal end of the trial sizer,
   wherein each of the plurality of spacers includes a first surface and a second surface with a lateral edge extending therebetween;
   the trial sizer further including:
      a gripping section proximate to a proximal end of the trial sizer;
      the distal end of the trial sizer configured to temporarily engage each of the plurality of spacers; and
      the universal guide body configured to reside between the distal end and the gripping section of the trial sizer;
   the universal guide body further including a pair of hollow instrument guides,
   wherein each of the pair of hollow instrument guides includes:
      a bore hole extending from a proximal end to a distal end of the respective one of the pair of hollow instrument guides, the bore hole having a longitudinal axis extending therebetween;
      the longitudinal axes of the bore holes in the pair of hollow instrument guides being non-parallel to a longitudinal axis of a respective one of the plurality of spacers when the respective one of the plurality of spacers is engaged with the trial sizer;
   each of the plurality of spacers having a different thickness extending between respective ones of the first and second surfaces of each spacer;
   each of the plurality of spacers configured to operably engage the distal end of the trial sizer such that the respective first surface of each of the plurality of spacers is at a same relative distance and orientation from the distal ends of the pair of hollow instrument guides when the respective one of the plurality of spacers is engaged with the trial sizer, such that the pilot holes are configured to be drilled at drilling locations on one of the vertebrae independent of the thickness of the respective one of the plurality of spacers;
   whereby the respective one of the plurality of spacers is configured to be inserted between two of the patient's vertebrae and the universal guide body is configured to guide a user to-the drilling locations on the one of the vertebrae.

7. The kit of claim 6, wherein each bore hole has a diameter sized to receive one of the fasteners intended for insertion into the patient's vertebrae, whereby each of the fasteners is configured to be inserted through a respective one of the bore holes in a respective one of the pair of hollow instrument guides to secure the fasteners in the patient's vertebrae without having to first remove the trial sizer from the patient.

8. The kit of claim 6, wherein the universal guide body can be removed from a rest of the trial sizer.

9. The kit of claim 8, wherein the universal guide body includes a hollow bore hole sized to receive a guide body receiving section of the trial sizer.

10. The kit of claim 6, wherein the pair of hollow instrument guides are angled towards each other moving in a distal direction.

11. The kit of claim 6, wherein each of the pair of hollow instrument guides further includes a cutout window proximate the distal end of the respective hollow instrument guide, whereby the cutout window provides a visual of any instruments within the respective hollow instrument guide prior to the instruments interacting with the patient's vertebrae.

12. A method of implanting a device within a patient, the method comprising the steps of:
   providing a trial sizer, the trial sizer including:
      a main body extending from a proximal end to a distal end;
      a spacer secured to the distal end of the main body, the spacer having a first surface and a second surface with a lateral edge extending therebetween, a proximal end and a distal end with a longitudinal axis extending therebetween, and the spacer being sized to reside between a patient's vertebrae;
      a guide body residing proximate to the spacer, the guide body including a pair of hollow instrument guides, wherein each hollow instrument guide includes:
         a bore hole extending from a proximal end to a distal end of the respective hollow instrument guide, the bore hole having a longitudinal axis extending therebetween;
         the longitudinal axes of the bore holes in the pair of hollow instrument guides being non-parallel to the longitudinal axis of the spacer;
   inserting the spacer into a cavity within the patient, such that the pair of hollow instrument guides are angled towards a first vertebra;
   inserting a drilling instrument within at least one of the pair of hollow instrument guides and drilling a pilot hole into the first vertebra;
   providing a first implantable interacting element, the first implantable interacting element having a main body and a thread receipt; and
   partially inserting a second interacting element into the pilot hole, wherein the second interacting element has a thread configured to engage the thread receipt of the first implantable interacting element;

following the partial insertion of the second interacting element, positioning the first implantable interacting element between a proximal end of the partially inserted second interacting element and the first vertebra; and inserting the second interacting element further within the first vertebra, such that the thread of the second interacting element engages the thread receipt of the first implantable interacting element, thereby securing the first implantable interacting element to the second interacting element.

13. The method of claim 12, further comprising:

rotating the trial sizer 180 degrees about the longitudinal axis of the spacer;

inserting the spacer into the cavity within the patient, such that the pair of hollow instrument guides are angled towards a second vertebra in the patient;

inserting the drilling instrument within the guide body and drilling additional pilot holes into the second vertebra;

removing the trial sizer; and inserting additional second interacting elements within the additional pilot holes.

14. The method of claim 13, further comprising inserting the additional second interacting elements further within the second vertebra, such that the threads of the additional second interacting elements engage additional thread receipts of the first implantable interacting element, thereby further securing the first implantable interacting element to the second vertebra.

15. The method of claim 12, wherein the partially inserting the second interacting element into the pilot hole further includes inserting the second interacting element through one of the pair of hollow instrument guides when the spacer is within the cavity within the patient.

* * * * *